US008470295B2

(12) United States Patent
Warren et al.

(10) Patent No.: US 8,470,295 B2
(45) Date of Patent: Jun. 25, 2013

(54) METHODS OF TREATMENT OF ANDROGENIC STEROIDAL HORMONE DEPENDENT CANCER WITH AUGER ELECTRON-EMITTING NUCLEOSIDE ANALOGS

(75) Inventors: Stephen L. Warren, Fort Collins, CO (US); James E. Matsuura, Fort Collins, CO (US); Michael J. Gerber, Denver, CO (US)

(73) Assignee: Peak Biosciences, Inc., Fort Collins, CO (US)

( * ) Notice: Subject to any disclaimer, the term of this patent is extended or adjusted under 35 U.S.C. 154(b) by 238 days.

(21) Appl. No.: 12/599,594

(22) PCT Filed: May 9, 2008

(86) PCT No.: PCT/US2008/006040
§ 371 (c)(1),
(2), (4) Date: Nov. 10, 2009

(87) PCT Pub. No.: WO2008/140808
PCT Pub. Date: Nov. 20, 2008

(65) Prior Publication Data
US 2010/0233081 A1    Sep. 16, 2010

Related U.S. Application Data

(60) Provisional application No. 60/917,226, filed on May 10, 2007.

(51) Int. Cl.
*A61K 51/00* (2006.01)
*A61K 38/00* (2006.01)
*A61P 5/24* (2006.01)
*A61P 35/00* (2006.01)

(52) U.S. Cl.
USPC .............. 424/1.73; 514/10.2; 514/19.5

(58) Field of Classification Search
None
See application file for complete search history.

(56) References Cited

U.S. PATENT DOCUMENTS

| | | | |
|---|---|---|---|
| 2,245,350 A | 6/1941 | Marshall | |
| 4,994,033 A | 2/1991 | Shockey et al. | |
| 5,077,034 A | 12/1991 | Kassis et al. | |
| 5,221,256 A | 6/1993 | Mahurkar | |
| 5,354,279 A | 10/1994 | Hofling | |
| 5,465,711 A | 11/1995 | Moll et al. | |
| 5,720,720 A | 2/1998 | Laske et al. | |
| 6,068,650 A | 5/2000 | Hofmann et al. | |
| 6,283,947 B1 | 9/2001 | Mirzaee | |
| 6,428,504 B1 | 8/2002 | Riaziat et al. | |
| 6,486,146 B1 * | 11/2002 | Zamoyski | 514/177 |
| 6,610,841 B1 | 8/2003 | Warren | |
| 6,627,176 B2 | 9/2003 | Perkins | |
| 6,703,050 B1 | 3/2004 | Brewer et al. | |
| 2001/0007933 A1 | 7/2001 | Lesh et al. | |
| 2001/0009970 A1 | 7/2001 | Chornenky et al. | |
| 2001/0031941 A1 | 10/2001 | Edwards et al. | |
| 2002/0002349 A1 | 1/2002 | Flaherty et al. | |
| 2002/0082559 A1 | 6/2002 | Chang et al. | |
| 2002/0123719 A1 | 9/2002 | Lavi et al. | |
| 2002/0133057 A1 | 9/2002 | Kukuk | |
| 2002/0133173 A1 | 9/2002 | Brock et al. | |
| 2003/0028147 A1 | 2/2003 | Aves et al. | |
| 2003/0093117 A1 | 5/2003 | Saadat | |
| 2003/0167031 A1 | 9/2003 | Odland | |
| 2003/0171738 A1 | 9/2003 | Konieczynski et al. | |
| 2004/0220606 A1 | 11/2004 | Goshgarian | |
| 2004/0243145 A1 | 12/2004 | Bobo et al. | |
| 2005/0069495 A1 * | 3/2005 | Baranowska-Kortylewicz et al. | 424/1.73 |
| 2005/0085715 A1 | 4/2005 | Dukesherer et al. | |
| 2005/0101823 A1 | 5/2005 | Linares et al. | |
| 2005/0107738 A1 | 5/2005 | Slater et al. | |
| 2005/0245858 A1 | 11/2005 | Miesel et al. | |
| 2006/0121085 A1 | 6/2006 | Warren et al. | |
| 2006/0206150 A1 | 9/2006 | Demarais et al. | |
| 2007/0038181 A1 | 2/2007 | Melamud et al. | |

(Continued)

FOREIGN PATENT DOCUMENTS

WO WO-2008020967 A2 2/2008
WO WO-2008020967 A3 2/2008

(Continued)

OTHER PUBLICATIONS

"International Application Serial No. PCT/US2008/006040, International Search Report and Written Opinion mailed Aug. 6, 2008", 12 pgs.

(Continued)

*Primary Examiner* — Elly-Gerald Stoica
(74) *Attorney, Agent, or Firm* — Schwegman Lundberg & Woessner, P.A.

(57) ABSTRACT

A method is provided for treatment of disorders involving hyperproliferative cells, such as malignancies, advanced stage solid tumors like glioblastoma multiforme, and non-malignant hyperproliferative pathological conditions such as adult macular degeneration. A short range, unselective cell killing radiotherapeutic substance is administered, optionally in a spatially defined volume of tissue, optionally in combination with a mitogenic agent that stimulates or induces DNA biosynthesis. In this way, the percentage of hyperproliferative that are susceptible to killing by the radiotherapeutic agent is increased. Cancer stem cells can be induced to enter S phase with the mitogenic agent, then killed with the radiotherapeutic agent. Thus, not only does the combination effectively kill the transit amplifying cell population, the most rapidly replicating type of cell in a tumor, but it also effectively kills the tumor stem cells, which give rise to the transit amplifying cells, for a longer lasting anticancer effect.

22 Claims, No Drawings

U.S. PATENT DOCUMENTS

| | | | |
|---|---|---|---|
| 2008/0177183 | A1 | 7/2008 | Courtney et al. |
| 2010/0222668 | A1 | 9/2010 | Dalke et al. |
| 2010/0280494 | A1 | 11/2010 | Matsuura et al. |
| 2011/0135569 | A1 | 6/2011 | Dalke et al. |

FOREIGN PATENT DOCUMENTS

| | | |
|---|---|---|
| WO | WO-2008/115566 A3 | 9/2008 |
| WO | WO-2008115511 A1 | 9/2008 |
| WO | WO-2008115566 A2 | 9/2008 |
| WO | WO-2008140808 A1 | 11/2008 |

OTHER PUBLICATIONS

"International Application Serial No. PCT/US2008/03711, Search Report mailed Jul. 28, 2008", 6 pgs.

"International Application Serial No. PCT/US2008/03711, Written Opinion mailed Jul. 28, 2008", 11 pgs.

Aft, R. L., et al., "Enhancing targeted radiotherapy by copper(II)diacetyl-bis (N4-methylthiosemicarbazone) using 2-deoxy-D-glucose.", Cancer Res., 63(17), (Sep. 1, 2003), 5496-504.

Bobo, R. H., et al., "Convection-enhanced delivery of macromolecules in the brain.", Proc Natl Acad Sci U S A., 91(6), (Mar. 15, 1994), 2076-80.

Hall, W. A., et al., "Convection-enhanced delivery in clinical trials.", Neurosurg Focus., 14(2), (Feb. 15, 2003), 1-4 (e2).

Hochberg, F. H., et al., "Assumptions in the radiotherapy of glioblastoma", Neurology, 30(9), (Sep. 1980), 907-11.

Mischel, Paul S., et al., "DNA-microarray analysis of brain cancer: molecular classification for therapy.", Nat Rev Neurosci., 5(10), (Oct. 2004), 782-92.

Mulford, D. A., et al., "The promise of targeted {alpha}-particle therapy.", J Nucl Med., 46 (Suppl 1), (Jan. 2005), 199S-204S.

Ohgaki, Hiroko, et al., "Genetic pathways to glioblastoma: a population-based study.", Cancer Res., 64(19), (Oct. 1, 2004), 6892-9.

Phillips, Heidi S, et al., "Molecular subclasses of high-grade glioma predict prognosis, delineate a pattern of disease progression, and resemble stages in neurogenesis.", Cancer Cell., 9(3), (Mar. 2006), 157-73.

Raghavan, Raghu, et al., "Convection-enhanced delivery of therapeutics for brain disease, and its optimization.", Neurosurg Focus, 20(4), (Apr. 15, 2006), E12.

Vijayakumar, S., et al., "Advances in Radiation Oncology", Lancet, 349 (suppl II), (May 1997), 1-3.

Westphal, Manfred, et al., "A phase 3 trial of local chemotherapy with biodegradable carmustine (BCNU) wafers (Gliadel wafers) in patients with primary malignant glioma.", Neuro Oncol., 5(2), (Apr. 2003), 79-88.

Yanik, G. A., et al., "Pilot study of iodine-131-metaiodobenzylguanidine in combination with myeloablative chemotherapy and autologous stem-cell support for the treatment of neuroblastoma.", J Clin Oncol., 20(8), (Apr. 15, 2002), 2142-9.

"U.S. Appl. No. 12/375,583, Non Final Office Action mailed Sep. 17, 2012", 20 pgs.

"U.S. Appl. No. 12/375,583, Response filed Dec. 14, 2012 to Non Final Office Action mailed Sep. 17, 2012", 28 pgs.

"U.S. Appl. No. 12/531,808, Non Final Office Action mailed Oct. 12, 2012", 25 pgs.

"U.S. Appl. No. 12/531,825, Final Office Action mailed Nov. 20, 2012", 14 pgs.

"U.S. Appl. No. 12/531,825, Non Final Office Action mailed Mar. 27, 2012", 24 pgs.

"U.S. Appl. No. 12/531,825, Response filed Jul. 26, 2012 to Non Final Office Action mailed Mar. 27, 2012", 24 pgs.

"U.S. Appl. No. 12/599,594, filed Nov. 10, 2009", 105 pgs.

"International Application Serial No. PCT/US2007/016701, International Search Report and Written Opinion mailed Sep. 16, 2008", 9 pgs.

"International Application Serial No. PCT/US2008/003582, Search Report mailed Jul. 2, 2008", 6 pgs.

"International Application Serial No. PCT/US2008/003582, Written Opinion mailed Jul. 2, 2008", 5 pgs.

Bloomer, W. F, et al., "Letter: Antineoplastic effect of iodine-125-labelled iododeoxyuridine.", Int J Radiat Biol Relat Stud Phys Chem Med., 27(5), (May 1975), 509-11.

Buchegger, Franz, et al., "Highly Efficient DNA Incorporation of Intratumourally Injected [125I]Iododeoxyuridine Under Thymidine Synthesis Blocking in Human Glioblastoma Xenografts", Int. J. Cancer: 110, (2004), 145-149.

Neshasteh-Riz, A, et al., "Incorporation of Idodeoxyuridine in Multicellular Glioma Spheroids: Implications for DNA-Targeted Radiotherapy Using Auger Electron Emitters", British Journal of Cancer, (1997), 493-499.

Reza, M. S, et al., "Iodo-2'-Deoxyuridine (IUdR) and 125IUdR Loaded Biodegradable Microspheres for Controlled Delivery to the Brain", J. Microencapsul, vol. 15, (1998), 789-801.

* cited by examiner

METHODS OF TREATMENT OF ANDROGENIC STEROIDAL HORMONE DEPENDENT CANCER WITH AUGER ELECTRON-EMITTING NUCLEOSIDE ANALOGS

CLAIM OF PRIORITY TO RELATED APPLICATIONS

This application is a U.S. National Stage Filing under 35U.S.C. 371 from International Patent Application Ser. No. PCT/US2008/006040, filed May 9, 2008, and published on Nov. 20, 2008, as WO 2008/140808 A1, which claims the priority benefit of U.S. Provisional Patent Application Ser. No. 60/917,226, filed May 10, 2007 (now expired), the contents of which are incorporated herein by reference in their entirety.

BACKGROUND

Locally advanced or locally invasive solid tumors are primary cancers that have extensively invaded or infiltrated into the otherwise healthy tissues surrounding the site where the tumor originated. Locally advanced tumors may arise in tissues throughout the body, but unlike early stage tumors may not be amenable to complete surgical excision or complete ablation using radiation treatments. Due to the invasion of the surrounding tissues by tumor processes, any surgical procedure that would serve to remove all the cancerous cells would also be likely to maim or destroy the organ in which the cancer originated. Similarly, radiation treatments intended to eradicate the cancerous cells left behind following surgery frequently lead to severe and irreparable damage to the tissues in and around the intended treatment field. Often, surgery is combined with radiotherapy, chemotherapy or a combination of adjuvant therapies designed to eliminate the malignant cells that could not be removed by the surgery. However, when a tumor has infiltrated into otherwise healthy tissues surrounding the site where the tumor originated, even combination treatments including surgery plus therapy, or surgery plus therapy plus chemotherapy may not be capable of eradicating the tumor cells without causing severe damage to the tissues in the treatment field.

In cases involving locally advanced tumors, surgery may be used for gross excision, a procedure referred to as "debulking," but the surgeon at present does not have the tools to eliminate individual tumor cells, microscopic tumor processes, or tumor-associated vasculature from the normal tissue surrounding the tumor excision site. It is often critical to minimize the volume of surrounding tissue that is excised in such operations. For example, in the case of tumors of the central nervous system, normal brain functions may be severely compromised as a result of tissue loss. Thus, in such cases surgery is often accompanied by radiation therapy and/or chemotherapy in an attempt to kill cancerous cells remaining in the surrounding brain tissue. The chemotherapy may be delivered to the residual tumor cells by a localized or systemic route of administration. By limiting the extent of surgical excision, and relying upon the adjunctive treatments to eliminate the residual cancer cells, the function of an organ may be preserved.

Conventional radiation therapy, using ionizing radiation beams (X-ray, gamma ray, or high energy beta particles), while well-established as an anti-cancer treatment modality, is not curative in the majority of patients whose cancer is locally advanced. Another form of radiation treatment is brachytherapy, the implantation of sealed radioactive sources emitting gamma rays or high energy beta particles within the tissue adjacent to the tumor site, for example in treatment of brain or prostate cancer. For example, see U.S. Pat. Nos. 6,248,057, 6,743,211, and 6,905,455.

Even with the combination of systemic agents and x-rays, nearly one third of patients with locally advanced solid tumors relapse locally without metastatic dissemination (Vijaykumar, S. and Hellman, S., "Advances in Radiation Oncology," Lancet, 349[S11]: 1-3 (1997)). Ionizing radiation, whether from a beam or from an isotopic implant emitting high energy radiation, lacks the specificity needed to eliminate the tumor cells while sparing the normal cells within the treatment field. Thus, collateral damage to normal tissues cannot be avoided. Conventional radiation therapy has several additional limitations. X-rays are administered by an intermittent schedule, usually daily for 5 days per week, thereby providing an opportunity for the cancer cells to repair their DNA and to repopulate the tumor between treatments. Ionizing radiation requires sufficient oxygen in the tissues to eliminate tumor cells, but most solid tumors are relatively hypoxic, and therefore inherently resistant to radiation. In addition, the total lifetime dose of radiation is limited by the risk of severe late toxicities. Therefore, with few exceptions only a single treatment course, usually lasting no more than 6-7weeks, can be administered to a tumor. Finally, ionizing radiation is itself oncogenic, especially when used in combination with chemotherapy agents.

Most types of chemotherapy also suffer from a lack of tumor specificity and also cause collateral damage to normal tissues, since chemotherapeutic agents are distributed throughout the body and exert their effects on normal cells as well as malignant cells. Many systemic chemotherapy agents act on cells undergoing DNA synthesis and cell division, and thus may impact many cell populations throughout the body in addition to the target cancer cells.

A recent development that is critical for understanding the underlying biology of locally advanced solid tumors is the discovery of cancer stem cells, a minority subpopulation of the cells that comprise a tumor. For example, see Jordan, C. T. et al. Cancer Stem Cells. N. Eng J. Med. 355:1253-61 (2006) and Al-Hajj M et al. Therapeutic implications of cancer stem cells. Current Opinion in Genetics and Development. 14:43-47 (2004). In most tumors examined, the cancer stem cells comprise no more than 1% of the total tumor cell population, and yet these cells are responsible for maintaining the growth of the entire tumor by virtue of their capacity for self renewal and extended proliferation. When transplanted into immuno-compromised rodents, only the cancer stem cells can form progressive tumors. In fact, cancer stem cells can recapitulate the distinctive microscopic architectural patterns characteristic of the original human tumor from which the cells were isolated.

Cancer stem cells are believed to proliferate rather slowly, and they represent only a small proportion of the cycling/dividing cells within a tumor (as observed at a given time). Cancer stem cells give rise to a more rapidly proliferating subpopulation of cancer cells, referred to as "transit-amplifying" or "progenitor" cancer cells, which comprise the vast majority of cycling/dividing cells observed in the tumor. The transit-amplifying cancer cells and cancer stem cells differ in multiple ways. Unlike the cancer stem cells, transit-amplifying cancer cells lack the capacity for self-renewal and undergo only a limited number of cell divisions before completely losing their proliferative capability. In contrast to cancer stem cells, transit-amplifying cancer cells cannot efficiently form progressive tumors when transplanted into immuno-compromised rodents.

Transit-amplifying cancer cells give rise to yet another subpopulation of cancer cells that cannot divide. These postmitotic cancer cells comprise the majority of cells in many solid tumors. Thus, solid tumors are comprised of at least three distinct subpopulations of malignant cells, each endowed with a different capacity for cell division and continuing growth. Indeed, the vast majority of cells in most solid tumors cannot support progressive tumor growth or lead to tumor recurrence after an initial remission or response to treatment.

The tumor-shrinking and/or tumor-inhibiting activities of ionizing radiation and currently used anticancer drugs are believed to involve direct effects on the transit-amplifying cancer cells, and in many cases the blood vessels that supply tumors (For example, see Jordan, C. T. et al. Cancer Stem Cells. N. Eng J. Med. 355:1253-61 [2006]; and Fidler I. J. et al. "Angiogenesis" pp 129-136 in Cancer Principles and Practice of Oncology 7$^{th}$ edition. De Vita V T, Hellmann S and Rosenberg S A. Lippincott Williams & Wilkins © 2005). Applying the principles of stem cell biology to cancer. Nature Reviews Cancer 3:895-902 (2003); and Polyak K and Hahn W C. Roots and Stems: stem cells in cancer. Nature Medicine. 11:296-300 (2006). Neither of these two major treatment modalities is capable of eradicating locally advanced solid tumors without causing severe damage to the tissues in which the cancer originated, or preventing the recurrence of locally advanced solid tumors without causing severe damage to the tissues in which the cancer originated; and neither of these major treatment modalities is capable of producing long term remissions of most types of locally advanced solid tumors, even when used in combination. Ionizing radiation and currently used drugs usually provide only a short term effect on tumor growth.

Cancer stem cells have been referred to as the "root" of the tumor, and accordingly, the elimination of transit-amplifying and postmitotic cancer cell subpopulations has been likened to "weed whacking", because it is invariably associated with re-growth of the tumor. The elimination of cancer stem cells is believed to be a prerequisite for curing advanced solid tumors, such as by identifying targeted agents that can selectively kill the cancer stem cells while sparing normal stem cells. For example see Pardal et al. Applying the principles of stem cell biology to cancer. Nature Reviews Cancer 3:895-902 (2003); Polyak K and Hahn W C. Roots and Stems: stem cells in cancer. Nature Medicine. 11:296-300 (2006); and Guzman M and Jordan C T. Considerations for targeting malignant stem cells in leukemia. Cancer Control. 11:97-104 (2004).

Cancer stem cells have been isolated and characterized in patients with many types of malignancies, including a particularly aggressive type of primary brain tumor referred to as "glioblastoma multiforme" or "GBM". For example see Singh, S. K. et. al. Identification of human brain tumour-initiating cells. Nature 432:396-399 (2004); Galli R., et. al. Isolation and characterization of tumorigenic, stem-like neural precursors from human glioblastoma. Cancer Res. 64:7011-21 (2004). Sanai, N., Alvarez-Buylla, A. and Berger, M. S. 2005. Neural Stem Cells and the Origin of Gliomas N. Engl J. Med. 353:811-22. Because tumor stem cells are responsible for the maintenance of GBM tumors, this subpopulation of cells must be eliminated to prevent tumor recurrence following treatment, and to achieve long term survival in patients with these tumors.

Killing brain tumor stem cells presents a formidable challenge. There are four major obstacles standing in the way. First, recent studies using gene expression profiling indicate that solid tumors, including GBM, are much more genetically and metabolically heterogeneous than previously anticipated. For example, see Quackenbush, J. Microarray Analysis and Tumor Classification. N Eng J Med. 354:2463-72 (2006); Mischel, P. S. Cloughesy, T. F. and Nelson, S. F., "DNA-Microarray Analysis of Brain Cancer: Molecular Classification for Therapy," Nature Cancer Reviews, 5:782-792 (2004). Solid tumors, as well as the cancer stem cells that drive their growth, appear to be genetically and metabolically heterogeneous despite a common organ or tissue of origin, and despite very similar appearances under the microscope. This is especially true of malignant gliomas, which arise in the central nervous system. For example, see Phillips et al. Molecular subclasses of high-grade glioma predict prognosis, delineate a pattern of disease progression, and resemble stages in neurogenesis. Cancer Cell 9:157-173 (2006). In view of the genetic/metabolic heterogeneity of solid tumors, biochemical targeting (i.e. the search for agents that specifically target the stem cells in each type of tumor) is a daunting challenge.

Second, brain tumor stem cells and other types of cancer stem cells are inherently resistant to chemotherapeutic agents, in part due to elevated expression of drug efflux transport proteins. For example, see Hirschmann-Jax C et al. A distinct "side population" of cells with high drug efflux capacity in human tumor cells. Proc. Natl. Acad. Sci. USA. 101; 14228-14233 (2004); Kondo T. et al Persistence of a small subpopulation of cancer stem-like cells in the C-6 glioma cell line. Proc. Nat. Acad. Sci. USA. 101: 781-786 (2004); and Jordan, C. T. et al. Cancer Stem Cells. N. Engl J. Med. 355:1253-61 (2006).

Third, brain tumor stem cells are resistant to ionizing radiation due to the preferential induction of DNA damage-response genes that repair DNA damage caused by radiation. For example, see Bao, S. et al. Glioma stem cells promote radioresistance by preferential activation of the DNA damage response. 2006. Nature 444:756-710.

Finally, brain tumor stem cells are believed to proliferate more slowly than other cell populations within the tumor thereby making them less susceptible to the toxic effects of cell cycle active agents and ionizing radiation. For example, see Jordan, C. T. et al. Cancer Stem Cell. N. Engl J. Med. 355:1253-61 (2006). Pardal et al. Applying the principles of stem cell biology to cancer. Nature Reviews Cancer 3:895-902 (2003); Polyak K and Hahn W C. Roots and Stems: stem cells in cancer; Nature Medicine. 11:296-300 (2006). Cancer stem cells are also believed to proliferate/cycle at a slower rate than their immediate progeny, the transit-amplifying cancer cells (see Vescovi A L et al. Brain Tumor Stem Cells. Nature Reviews—Cancer, 6:425-436 (2006); Sanai N et al. Neural Stem Cells and the Origin of Gliomas. N Eng J Med 353 811 (2005); and Singh et al. Cancer stem cells in nervous system tumors. Oncogene, 23, 7267-7273 (2004). These challenges notwithstanding, tumor stem cells represent a defined cellular target for new anticancer treatments.

Certain drugs can block the progression of tumor cells out of S-phase, thus effectively increasing the fraction of susceptible cells within the target cell population. For example, see Chu E. "Principles of Medical Oncology", pp 295-306 in Cancer Principles and Practice of Oncology 7$^{th}$ edition. De Vita V T, Hellmann S and Rosenberg S A eds. Lippincott Williams & Wilkins © 2005. Combining a cell-cycle inhibitory agent with an S-phase active cytotoxic agent is a well established treatment principle. In fact, this approach has been used successfully using a cell cycle inhibitor, 5-fluorouridine 2' deoxyribonucleoside, to increase the uptake and incorporation of $^{125}$IUDR into DNA. For example, see: Holmes, J. M. The toxicity of fluorodeoxyuridine when used to increase the uptake of $^{125}$I-iododeoxyuridine into tissue culture cells in vitro. J Comp Pathol. 93:531-539 (1983); F. Buchegger et al Highly efficient DNA incorporation of intratumourally injected [$^{125}$I]iododeoxyuridine under thymidine synthesis blocking in human glioblastoma xenografts. Int J Cancer 110:145-149 (2004); and Perillo-Adamer, F. Short fluorodeoxyuridine exposure of different human glioblastoma lines induces high-level accumulation of S-phase cells that avidly incorporate $^{125}$I-iododeoxyuridine. Eur J Nucl Med Mol Imaging 33: 613-620 (2006). This approach is unlikely to be amenable to cancer stem cells, which may not proliferate with sufficient rapidity to be susceptible to cell cycle blockade.

Another treatment strategy is to combine a mitogenic growth factor with an S-phase active cytotoxic agent; however, in practice, this approach has not been particularly useful. One problem has been that numerous mitogenic growth factors have the potential to stimulate the growth of tumors, which counteracts the desired effect of the treatment (i.e. tumor shrinkage). Another problem is that the addition of a mitogenic growth factor to an S-phase active cytotoxic agent may increase the toxicity of the cytotoxic agent towards cycling cells in normal tissues, including normal stem cells and normal transit-amplifying cells in the brain, bone marrow, oral mucosa, gut, skin, hair and/or germ cells. For example, while FGF-2, EGF and PDGF may cause tumor stem cells to enter S-phase of the cell cycle (i.e. initiate DNA synthesis), these mitogenic growth factors may also stimulate normal neural progenitor cells to enter S-phase in various regions of the CNS (see Palmer T D et al. Fibroblast growth factor-2 activates a latent neurogenic program in neural stem cells from diverse regions of the adult CNS. J. Neurosci. 19: 8487-8497 [1999]; Jackson, E L et al. PDGF-alpha positive B cells are neural stem cells in the adult SVZ that form glioma like growths in response to increased PDGF signaling. Neuron 51:187-199 [2006]; and Gritti, A et al. Epidermal and Fibroblast Growth Factors Behave as Mitogenic Regulators for a Single Multipotent Stem Cell-Like Population from the Subventricular Region of the Adult Mouse Forebrain J. Neurosci, 19:3287-3297 [1999]).

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. It is the leading cause of central vision loss (blindness) in the United States today for those over the age of fifty years. Although some macular dystrophies that affect younger individuals are sometimes referred to as macular degeneration, the term generally refers to adult or age-related macular degeneration (AMD or ARMD).

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Until recently, no effective treatments were known for wet macular degeneration. However, new drugs, called anti-angiogenics or anti-VEGF (anti-Vascular Endothelial Growth Factor) agents, when injected directly into the vitreous humor of the eye using a small needle, can inhibit growth of abnormal blood vessels and improvement of vision. The injections usually have to be repeated on a monthly or bi-monthly basis. Examples of these agents include anti-VEGF antibodies (Lucentis and Avastin) and anti-VEGF apatamers (e.g. Macugen).

A unique cell killing mechanism that has garnered considerable interest is the release of Auger electrons. These electrons are emitted by radionuclides that decay by electron capture and internal conversion. Examples of Auger emitting radionuclides include $^{123}$Iodine, $^{124}$Iodine $^{125}$Iodine, $^{77}$Bromine, $^{80m}$Bromine and $^{211}$Astatine. Auger electrons have energies even lower than the energy of the beta particle emitted by tritium. This effect is amplified, because some Auger emitters release multiple electrons with each nuclear transformation. The low energy of the Auger electrons results in extremely short particle path lengths within tissues, which is highly desirable, because it minimizes collateral damage.

One molecular entity incorporating $^{125}$Iodine is [$^{125}$I]-iodouridine-deoxyriboside ($^{125}$IUDR), a thymidine analog. $^{125}$IUDR is recognized by DNA polymerases as a normal thymidine metabolite, and thus is incorporated into the chromosomes at times of DNA synthesis. Once incorporated into the DNA, the Auger electrons, with their very short range (often less than 10 nm), have access to the chemical backbone of the DNA duplex. For example, see Martin R F and Haseltine W A. Range of radiochemical damage to DNA with decay of Iodine-125. Science 213:896-898 (1981); and Kassis A I et al. Kinetics of uptake, retention, and radiotoxicity of $^{125}$IUDR in mammalian cells: implications of localized energy deposition by Auger processes. Radiation Research 109:78-89 (1987). When the $^{125}$Iodine atom disintegrates, Auger electrons have the potential to cause severe damage to chromosomes with minimal effect on cells in the immediate vicinity of the target cell. For example, see U.S. Pat. No. 5,077,034. $^{125}$IUDR also releases high energy gamma photons during internal conversion; therefore, this agent has the potential to damage DNA by two very different types of radiation.

Despite the recognition that $^{125}$IUDR has a unique cell killing capability, and despite many years of research aimed at exploiting this mechanism of action, including the concept of directly introducing $^{125}$IUDR into tumors (for example, see Kassis et. al. Treatment of tumors with 5-radioiodo-2'-deoxyuridine. U.S. Pat. No. 5,077,034), these agents have not been successfully applied to the treatment of cancer. The delivery of $^{125}$IUDR and related agents to solid tumors, using systemic or local administration, has proven to be extremely challenging. New approaches are needed to deliver $^{125}$IUDR (and related compounds) to solid tumors with the intent to eliminate the tumor-maintaining stem cells while at the same time sparing normal tissues that have been invaded by the cancer cells. This includes novel devices to deliver such agents directly into the tumors, and into the normal tissues that have been invaded by tumor cells, as described in Matsuura and Warren (Catheter and array for anticancer therapy (U.S. patent application Ser. No. 60/895,916). In addition, $^{125}$IUDR has not been used to treat non-neoplastic disorders characterized by pathological, unwanted cell proliferation.

In various embodiments the bioactive agent can include Auger-electron emitting radionucleoside or an analog or a prodrug thereof, such as a halogenated nucleoside analog, for example 5-[$^{123}$I]-iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine-2'-deoxyribonucleoside, 5-[$^{77}$Br]-bromoadenine 2'-deoxyribonucleoside, 5-[$^{80m}$Br]-bromoadenine 2'-deoxyribonucleoside, 5-[$^{211}$At]-astatouridine 2'-deoxyribonucleoside, or 8-[$^{211}$At]-astatoadenine 2'-deoxyribonucleoside. In various embodiments the bioactive agent can include an Auger-electron emitting nucleoside prodrug, such as a 3'- or 5'-phosphate or carboxylate ester of a deoxyribosyl or ribosyl moiety of the radionucleoside. In various embodiments, the bioactive agent can include a second medicament, such as an anticancer drug, an antiinflammatory drug, or an antibiotic.

Coadministration of mitogens and S-phase active agents, e.g. $^{125}$IUDR and other radionucleosides, as a method to eliminate neoplastic and non-neoplastic pathological cell proliferation, has not been feasible without exposing normal stem cells, e.g. resident populations in the brain, bone marrow, oral mucosa, gut, skin, hair, and germ cells, to such potentially lethal combinations.

SUMMARY

In various embodiments, the present invention is directed to a method of treatment of a malcondition in a patient characterized by a hyperproliferation of cells, comprising administering to a tissue of the patient comprising hyperproliferative cells a radiotherapeutic agent characterized by a short-range cytotoxic radioactive emission.

In various embodiments the malcondition can comprise a cancer, such as a solid tumor.

In various embodiments the malcondition can comprise a noncancerous hyperproliferative condition, such as macular degeneration.

In various embodiments, the radiotherapeutic agent can comprise an Auger electron emitting radioisotope, such as $^{125}$I.

In various embodiments, the radiotherapeutic agent can comprise a radiolabeled nucleoside analog, such as $^{125}$I-IUDR.

In various embodiments, the radiotherapeutic agent can be administered to a spatially defined volume of tissue, such as intratumorally.

In various embodiments, the radiotherapeutic agent can be administered to a spatially defined volume of tissue, such as intraocularly.

In various embodiments, the radiotherapeutic agent can be administered with a mitogenic agent. The mitogenic agent can be adapted to induce S phase in cells, such as in cancer stem cells, to stimulate a population of cells into cell division and/or to bring a population of cells into synchronous cell division.

In various embodiments, the radiotherapeutic agent can be administered with a mitogenic agent. The mitogenic agent can be adapted to induce S phase in cells, such as vascular endothelial cells, to stimulate a population of cells into cell division and/or to bring a population of cells into synchronous cell division.

In various embodiments, the mitogenic agent can be a growth factor, a hormone, a neuropeptide or neurohormone, a chemokine, a differentiation factor, a TNF-family ligand, an interleukin, or any combination thereof, or a peptide predicted from a transcribed locus for a growth factor, a hormone, a neuropeptide or neurohormone, a chemokine, a differentiation factor, a TNF-family ligand, or an interleukin. In various embodiments this administration can be performed locally. In various other embodiments this administration can be performed systemically.

In various embodiments, the radiotherapeutic agent, the mitogenic agent, or both, can be administered continuously, intermittently, or periodically. In various embodiments the radiotherapeutic agent and the mitogenic agent can be administered concurrently, sequentially, intermittently, or periodically, either together or at different times. In various embodiments this administration can be performed locally. In various other embodiments this administration can be performed systemically.

In various embodiments, the malcondition can include a cancer, a solid tumor, an advanced stage solid tumor, a glioblastoma multiforme, lymphoma, leukemia, or a non-neoplastic, but pathological, tissue hyperplasia, such as age-related macular degeneration, or a prostatic hyperplasia.

DETAILED DESCRIPTION OF THE INVENTION

As discussed above the tumor stem cells are the "root" of the cancer, but are difficult to eliminate due to metabolic and genetic heterogeneity, cancer cell resistance to various drugs in part caused by elevated levels of drug transport proteins, are often resistant to ionizing radiation, and proliferate more slowly than other cell populations. Tumor stem cells are typically characterized by a slow proliferation relative to the rate of mitosis and proliferation that characterizes cell types such as transit-amplifying or progenitor cells that are derived from tumor stem cells, and make up the bulk of the dividing cells in a tumor or other hyperproliferative malcondition.

Accordingly, the present invention is directed to a method that increases the susceptibility of tumor stem cells and transit amplifying or progenitor cells to agents that act most effectively during a stage in the cell's reproductive cycle characterized by high rates of DNA biosynthesis. One such stage, that takes place prior to formation of the mitotic spindle and chromosome separation, is referred to as the "S phase." Embodiments of the inventive method provide for the use of a DNA synthesis inducing agent, a mitogen. In hormone-responsive cells, for example in prostate cancer, the mitogen can be a hormone. Or, the mitogen can be growth factor, a neuropeptide or neurohormone, a chemokine, a differentiation factor, a TNF-family ligand, an interleukin, or can be a peptide predicted from a transcribed locus for a growth factor, a hormone, a neuropeptide or neurohormone, a chemokine, a differentiation factor, a TNF-family ligand, or an interleukin.

It is generally accepted that agents that induces or stimulates cells to enter a cellular stage comprising DNA biosynthesis, such as growth factors, would be contraindicated in cancer patients due to their ability to promote or augment the growth of the cancer cells or tumor associated neovascular cells, and/or due to the increased risk of toxicity to normal cells when coadministered with S-phase active agents. However, the inventors herein surprisingly recognize that there is reason to include the use of such agents when administered in conjunction with an agent that unselectively kills, with high efficiency, cells which take up the toxic agent at a high rate when the cell is in a cellular stage involving a high rate of DNA biosynthesis. A type of agent that can kill a cell unselectively, independent of its genetic profile, with high efficiency, and with little or no damage to adjacent cells has been identified by the inventors herein as including Auger electron emitting radiolabeled organic compounds that are adapted to be taken up and incorporated by cells undergoing DNA biosynthesis and cell division. In different embodiments of this invention, the physically restricted delivery of the radiotherapeutic substance and/or the mitogenic substance provided by a drug delivery mechanism to prevents or limits toxicity to normal proliferating tissues.

In the case of tumor stem cells which give rise to the other tumor cell types, while hyperproliferative, they typically divide at a lower rate than do their immediate progeny, transit amplifying or progenitor cells. Accordingly, by use of the agent that induces or stimulates cells to enter a cellular stage comprising DNA biosynthesis, a higher percentage of the total population of tumor stem cells can be brought into the portion of the cell cycle involving DNA biosynthesis at any given time. This can serve to shorten the time over which the unselective toxic agent, such as the radiotherapeutic substance, needs to be administered. In turn, a shortened period of administration will reduce the collateral damage caused to normal cells that happen to also be undergoing DNA biosynthesis at that time.

The treatment of hyperproliferating tissue either alone with an unselective radiotherapeutic substance or in combination with an agent that induces DNA biosynthesis, can be administered directly to the tissue including hyperproliferative cells, such as tumors or vascular tissue. The radiotherapeutic substance alone or in combination can be administered by simple injection, either concurrently or sequentially. Alternatively, the radiotherapeutic substance alone or in combination can be administered by means of bioerodible filaments, as described in patent application PCT/US2007/015549, filed Jul. 6, 2007 by the inventors herein, which is incorporated by reference herein in its entirety. Alternatively, the radiotherapeutic substance alone or in combination can be administered by means of an implanted catheter or catheter array, or by using convection enhanced delivery, as are described in patent applications PCT/US US2007/016701, filed Jul. 25, 2007, PCT/US2008/003711, filed Mar. 20, 2008, and PCT/US2008/003582, filed Mar. 19, 2008, all by the inventors herein, which are all incorporated by reference in their entireties.

Because $^{125}$IUDR damages chromosomes only after it is incorporated into DNA, this agent might have less activity against the stem cell subpopulation as compared to the transit amplifying cancer cells in the tumor, due to the lower rate of cell division among the stem cells than among their progeny transit amplifying cells. The inventors herein have recognized that it would be advantageous to increase the proportion of tumor stem cells that are engaged in S-phase DNA biosynthesis, so that a higher proportion of these cells may be rendered sensitive to the DNA-damaging effects of $^{125}$IUDR when incorporated into a cell's chromosomes.

As discussed above, administration of an S phase inducing agent, a mitogenic agent, to a patient afflicted with a malignancy, would generally be considered to be medically contraindicated, as most anticancer therapies aim at reducing, not increasing, a proportion of cells within a tumor that are undergoing mitosis. However, the inventors herein have surprisingly recognized that using the inventive method herein, such agents are desirable because they increase the vulnerability of the tumor stem cells and transit-amplifying or progenitor cells, in particular, to the unselective killing effects of the co-administered short-range radiotherapeutic substances. An alternate embodiment includes physical localization of the delivery of the radiotherapeutic agent either alone or in combination with systemic or local administration of the S-phase inducing agent. This physical localization is key to reduce the risk of systemic toxicities.

Agents capable of stimulating new rounds of DNA synthesis (i.e. S-phase) in the target cell population include mitogenic growth factors and derivatives; mitogenic proteins and peptide ligands; mitogenic antibodies; hormones and other mitogenic compounds. Preferred mitogenic agents include growth factors that stimulate cancer stem cells to proliferate in the brain and/or other primary tumor sites. Numerous growth factors have the ability to stimulate proliferation/cycling in normal stem cells and/or normal transit-amplifying cells, and some of these growth factors seem to have the same effects on cancer stem cells and/or their immediate progeny. For example see Reardon D A et al. Recent advances in the treatment of malignant astrocytoma. J. Clin Oncol. 8:1253-1265 (2006); Vescovi A L et al. Brain Tumor Stem Cells. Nature Reviews—Cancer, 6:425-436 (2006); Sanai N et al. Neural Stem Cells and the Origin of Gliomas. N Eng J Med 353 811 (2005); Singh et al. Cancer stem cells in nervous system tumors. Oncogene, 23, 7267-7273 (2004); Wechsler-Reya R and Scott M P. The developmental biology of brain tumors. Annu. Rev. Neurosci. 24:385-428 (2001); Gritti, A et al. Epidermal and Fibroblast Growth Factors Behave as Mitogenic Regulators for a Single Multipotent Stem Cell-Like Population from the Subventricular Region of the Adult Mouse Forebrain J. Neurosci, 19:3287-3297 (1999); Mellinghoff I K et al. Molecular determinants of the response to glioblastoma multiforme to EGFR inhibitors. N Eng J. Med. 353:2012-2024 (2005); Holland E C and Varmus H E. Basic fibroblast growth factor induces cell migration and proliferation after glia-specific gene transfer in mice. Proc. Natl. Acad. Sci. USA. 95: 1218-1223 (1998); Purow B W et al. Expression of notch-1 and its ligands delta-1-like and jagged-1, is critical for glioma cell survival and proliferation. Cancer Res. 65:2353-2362 (2005); Liau L M et al. Identification of a human glioma-associated growth factor gene, granulin, using differential immunoabsorption. Cancer Res. 60:1353-1360 (2000); Le Bras B et al. VEGF-C is a trophic factor for neural progenitors in the vertebrate embryonic brain. Nature Neuroscience 9: 340-348 (2006); Erlandsson A et al. Stem cell factor is a chemoattractant and a survival factor for CNS stem cells. Exp. Cell Res. 101:201-210 (2004); Jin K et al. Stem cell factor stimulates neurogenesis in vitro and in vivo. J. Clin Investigation. 110:311-319 (2002); Ahn S. and Joyner A. In vivo analysis of quiescent adult neural stem cells responding to Sonic Hedgehog. Nature 437:894-897 (2005); Barbero S et al. Stromal cell-derived factor 1 alpha stimulates human glioblastoma cell growth through activation of both extracellular signal-regulated kinases ½ and AKT. Cancer Res. 63: 1969-1974 (2003); Zhou Y et al. CXCR4 is a major chemokine receptor on glioma cells and mediates their survival. J. Biol. Chem. 277:49481-49487 (2002); Jackson, E L et al. PDGF-alpha positive B cells are neural stem cells in the adult SVZ that form glioma like growths in response to increased PDGF signaling. Neuron 51:187-199 (2006).

The present invention discloses numerous mitogenic growth factors and other mitogenic proteins to be used in combination with short-range unselective high efficiency killing radiotherapeutic substances such as Auger electron emitting radionucleoside analogs including $^{125}$IUDR and related compounds. Some mitogenic growth factors include EGF, TGF-α, PDGF, basic FGF, FGF2, VEGF, VEGF-C, stem cell factor, Stromal cell-derived factor 1 alpha, DLL-1, DLL-2, DLL-3, JAG-1, Sonic Hedgehog, IGF-1, IGF-2, KGF, HGF, c-kit ligand and granulin. Many additional growth factors, hormones, and other potentially mitogenic proteins are listed below:

Growth Factors
EGF: Epidermal growth factor (beta-urogastrone)/Hs.419815
TGFA: Transforming growth factor, alpha/Hs.170009
1FGF1: Fibroblast growth factor 1 (acidic)/Hs.483635

2FGF2: Fibroblast growth factor 2 (basic)/Hs.284244
3FGF3: Fibroblast growth factor 3/Hs.37092
4FGF4: Fibroblast growth factor 4/Hs.1755
5FGF5: Fibroblast growth factor 5/Hs.37055
6FGF6: Fibroblast growth factor 6/Hs.166015
7FGF7: Fibroblast growth factor 7 (keratinocyte growth factor)/Hs.567268
8FGF8: Fibroblast growth factor 8 (androgen-induced)/Hs.57710
9FGF9: Fibroblast growth factor 9 (glia-activating factor)/Hs.111
10FGF10: Fibroblast growth factor 10/Hs.248049
11FGF11: Fibroblast growth factor 11/Hs.380704
12FGF12: Fibroblast growth factor 12/Hs.584758
13FGF13: Fibroblast growth factor 13/Hs.6540
14FGF14: Fibroblast growth factor 14/Hs.651136
16FGF16: Fibroblast growth factor 16/Hs.537037
17FGF17: Fibroblast growth factor 17/Hs.248192
18FGF18: Fibroblast growth factor 18/Hs.87191
19FGF19: Fibroblast growth factor 19/Hs.249200
20FGF20: Fibroblast growth factor 20/Hs.199905
21FGF21: Fibroblast growth factor 21/Hs.283015
22FGF22: Fibroblast growth factor 22/Hs.248087
23FGF23: Fibroblast growth factor 23/Hs.287370
FGFBP1: Fibroblast growth factor binding protein 1/Hs.1690
FGFBP2: Fibroblast growth factor binding protein 2/Hs.98785
FGFBP3: Fibroblast growth factor binding protein 3/Hs.591917
KGFLP1: Keratinocyte growth factor-like protein 1/Hs.439341
KGFLP2: Keratinocyte growth factor-like protein 2/Hs.652376
LOC728195: Similar to KGF precursor (Fibroblast growth factor 7) (HBGF-7)/Hs.648152
PDGFA: Platelet-derived growth factor alpha polypeptide/Hs.645488
PDGFB: Platelet-derived growth factor beta polypeptide/Hs.1976
PDGFC: Platelet derived growth factor C/Hs.570855
PDGFD: Platelet derived growth factor D/Hs.352298
LOC729619: Similar to Platelet-derived growth factor A chain precursor (PDGF A-chain) (PDGF-1)/Hs.632644
KITLG: KIT ligand/Hs.1048
HBEGF: Heparin-binding EGF-like growth factor/Hs.799
HGF: Hepatocyte growth factor (hepapoietin A; scatter factor)/Hs.396530
MST1: Macrophage stimulating 1 (hepatocyte growth factor-like)/Hs.349110
HDGF: Hepatoma-derived growth factor (high-mobility group protein 1-like)/Hs.506748
HDGF2: Hepatoma-derived growth factor-related protein 2/Hs.43071
HDGFL1: Hepatoma derived growth factor-like 1/Hs.97124
HDGFRP3: Hepatoma-derived growth factor, related protein 3/Hs.513954
LOC727738: Similar to Amphiregulin precursor (AR) (Colorectum cell-derived growth factor)/Hs.645475
AREG: Amphiregulin (schwannoma-derived growth factor)/Hs.270833
CTGF: Connective tissue growth factor/Hs.591346
TDGF1: Teratocarcinoma-derived growth factor 1/Hs.385870
GFER: Growth factor (ERV1 homolog, S. cerevisiae)/Hs.27184
GFI1: Growth factor independent 1/Hs.73172
EGFL6: EGF-like-domain, multiple 6/Hs.12844
VEGFA: Vascular endothelial growth factor A/Hs.73793
VEGFB: Vascular endothelial growth factor B/Hs.78781
VEGFC: Vascular endothelial growth factor C/Hs.435215
VGF: VGF nerve growth factor inducible/Hs.587325
PGF: Placental growth factor, vascular endothelial growth factor-related protein/Hs.252820
FIGF: C-fos induced growth factor (vascular endothelial growth factor D)/Hs.11392
ECGF1: Endothelial cell growth factor 1 (platelet-derived)/Hs.592212
CYR61: Cysteine-rich, angiogenic inducer, 61/Hs.8867
IGF1: Insulin-like growth factor 1 (somatomedin C)/Hs.160562
IGF2: Insulin-like growth factor 2 (somatomedin A)/Hs.373908
IGFALS: Insulin-like growth factor binding protein, acid labile subunit/Hs.839
IGFBP1: Insulin-like growth factor binding protein 1/Hs.642938
IGFBP2: Insulin-like growth factor binding protein 2, 36 kDa/Hs.438102
IGFBP3: Insulin-like growth factor binding protein 3/Hs.450230
IGFBP4: Insulin-like growth factor binding protein 4/Hs.462998
IGFBP5: Insulin-like growth factor binding protein 5/Hs.635441
IGFBP6: Insulin-like growth factor binding protein 6/Hs.274313
IGFBP7: Insulin-like growth factor binding protein 7/Hs.479808
IGFBPL1: Insulin-like growth factor binding protein-like 1/Hs.349705
IGFL1: IGF-like family member 1/Hs.546554
IGFL2: IGF-like family member 2/Hs.99376
IGFL3: IGF-like family member 3/Hs.365496
IGFL4: IGF-like family member 4/Hs.531310
INSL3: Insulin-like 3/Hs.37062
INSL4: Insulin-like 4 (placenta)/Hs.418506
INSL5: Insulin-like 5/Hs.251380
INSL6: Insulin-like 6/Hs.632648
RLN3: Relaxin 3/Hs.352155
Neuropeptides, Neurohormones, Hormones and Related Proteins
NGFB: Nerve growth factor, beta polypeptide/Hs.2561
PTN: Pleiotrophin (heparin binding growth factor 8, neurite growth-promoting factor 1)/Hs.371249
TPPP: Brain-specific protein p25 alpha/Hs.591746
NPB: Neuropeptide B/Hs.591139
NPFF: Neuropeptide FF-amide peptide precursor/Hs.104555
NPS: Neuropeptide S/Hs.643423
NPW: Neuropeptide W/Hs.233533
NPY: Neuropeptide Y/Hs.1832
NRG1: Neuregulin 1/Hs.453951
NRP1: Neuropilin 1/Hs.131704
NRP2: Neuropilin 2/Hs.471200
NTF3: Neurotrophin 3/Hs.99171
NTF5: Neurotrophin 5 (neurotrophin 4/5)/Hs.266902
NTN2L: Netrin 2-like (chicken)/Hs.634941
TAC1: Tachykinin, precursor 1 (substance K, substance P, neurokinin 1, neurokinin 2, neuropeptide K, neuropeptide gamma)/Hs.2563
AMH: Anti-Mullerian hormone/Hs.112432
AVP: Arginine vasopressin (neurophysin II, antidiuretic hormone)/Hs.89648
CALCA: Calcitonin/calcitonin-related polypeptide, alpha/Hs.37058

CRH: Corticotropin releasing hormone/Hs.75294
CRHBP: Corticotropin releasing hormone binding protein/Hs.115617
CSH1: Chorionic somatomammotropin hormone 1 (placental lactogen)/Hs.406754
FSHB: Follicle stimulating hormone, beta polypeptide/Hs.36975
GAST: Gastrin/Hs.2681
GHRH: Growth hormone releasing hormone/Hs.37023
GHRL: Ghrelin/obestatin preprohormone/Hs.590080
GNRH1: Gonadotropin-releasing hormone 1 (luteinizing-releasing hormone)/Hs.82963
GNRH2: Gonadotropin-releasing hormone 2/Hs.129715
GPHA2: Glycoprotein hormone alpha 2/Hs.436119
GPHB5: Glycoprotein hormone beta 5/Hs.375028
GRTP1: Growth hormone regulated TBC protein 1/Hs.170904
HCRT: Hypocretin (orexin) neuropeptide precursor/Hs.158348
LHB: Luteinizing hormone beta polypeptide/Hs.154704
PMCH: Pro-melanin-concentrating hormone/Hs.646410
POMC: Proopiomelanocortin (adrenocorticotropin/beta-lipotropin/alpha-melanocyte stimulating hormone/beta-melanocyte stimulating hormone/beta-endorphin)/Hs.1897
PRLH: Prolactin releasing hormone/Hs.247710
PTH: Parathyroid hormone/Hs.37045
PTHB1: Parathyroid hormone-responsive B1/Hs.372360
PTHLH: Parathyroid hormone-like hormone/Hs.591159
TRH: Thyrotropin-releasing hormone/Hs.182231
TSHB: Thyroid stimulating hormone, beta/Hs.406687
Differentiation Factors and Related Proteins
TGFB1: Transforming growth factor, beta 1/Hs.645227
TGFB2: Transforming growth factor, beta 2/Hs.133379
TGFB3: Transforming growth factor, beta 3/Hs.592317
TBRG1: Transforming growth factor beta regulator 1/Hs.436410
TBRG4: Transforming growth factor beta regulator 4/Hs.231411
LTBP1: Latent transforming growth factor beta binding protein 1/Hs.49787
LTBP2: Latent transforming growth factor beta binding protein 2/Hs.512776
LTBP3: Latent transforming growth factor beta binding protein 3/Hs.289019
LTBP4: Latent transforming growth factor beta binding protein 4/Hs.466766
BMP1: Bone morphogenetic protein 1/Hs.1274
BMP2: Bone morphogenetic protein 2/Hs.73853
BMP3: Bone morphogenetic protein 3 (osteogenic)/Hs.121507
BMP4: Bone morphogenetic protein 4/Hs.68879
BMP15: Bone morphogenetic protein 15/Hs.532692
BMP5: Bone morphogenetic protein 5/Hs.296648
BMP6: Bone morphogenetic protein 6/Hs.285671
BMP7: Bone morphogenetic protein 7 (osteogenic protein 1)/Hs.473163
BMP8A: Bone morphogenetic protein 8a/Hs.472497
BMP10: Bone morphogenetic protein 10/Hs.158317
LIF: Leukemia inhibitory factor (cholinergic differentiation factor)/Hs.2250
GDF2: Growth differentiation factor 2/Hs.279463
GDF3: Growth differentiation factor 3/Hs.86232
GDF5: Growth differentiation factor 5 (cartilage-derived morphogenetic protein-1)/Hs.1573
GDF6: Growth differentiation factor 6/Hs.492277
GDF7: Growth differentiation factor 7/Hs.447688
GDF8: Growth differentiation factor 8/Hs.41565
GDF9: Growth differentiation factor 9/Hs.25022
GDF10: Growth differentiation factor 10/Hs.2171
GDF11: Growth differentiation factor 11/Hs.643604
GDF15: Growth differentiation factor 15/Hs.616962
NRG1: Neuregulin 1/Hs.453951
DDEF1: Development and differentiation enhancing factor 1/Hs.106015
DDEF2: Development and differentiation enhancing factor 2/Hs.555902
DDEFL1: Development and differentiation enhancing factor-like 1/Hs.437379
EDF1: Endothelial differentiation-related factor 1/Hs.174050
CLCF1: Cardiotrophin-like cytokine factor 1/Hs.502977
Chemokines and Related Proteins
CCBP2: Chemokine binding protein 2/Hs.24286
CCL1: Chemokine (C—C motif) ligand 1/Hs.72918
CCL11: Chemokine (C—C motif) ligand 11/Hs.54460
CCL13: Chemokine (C—C motif) ligand 13/Hs.414629
CCL15: Chemokine (C—C motif) ligand 15/Hs.272493
CCL16: Chemokine (C—C motif) ligand 16/Hs.10458
CCL17: Chemokine (C—C motif) ligand 17/Hs.546294
CCL18: Chemokine (C—C motif) ligand 18/Hs.143961
CCL19: Chemokine (C—C motif) ligand 19/Hs.50002
CCL2: Chemokine (C—C motif) ligand 2/Hs.303649
CCL20: Chemokine (C—C motif) ligand 20/Hs.75498
CCL21: Chemokine (C—C motif) ligand 21/Hs.57907
CCL22: Chemokine (C—C motif) ligand 22/Hs.534347
CCL23: Chemokine (C—C motif) ligand 23/Hs.169191
CCL24: Chemokine (C—C motif) ligand 24/Hs.247838
CCL25: Chemokine (C—C motif) ligand 25/Hs.310511
CCL26: Chemokine (C—C motif) ligand 26/Hs.131342
CCL27: Chemokine (C—C motif) ligand 27/Hs.459590
CCL28: Chemokine (C—C motif) ligand 28/Hs.334633
CCL3: Chemokine (C—C motif) ligand 3/Hs.514107
CCL3L1: Chemokine (C—C motif) ligand 3-liked/Hs.512683
CCL4: Chemokine (C—C motif) ligand 4/Hs.75703
CCL4L2: Chemokine (C—C motif) ligand 4-like 2/Hs.449862
CCL5: Chemokine (C—C motif) ligand 5/Hs.514821
CCL7: Chemokine (C—C motif) ligand 7/Hs.251526
CCL8: Chemokine (C—C motif) ligand 8/Hs.652137
CX3CL1: Chemokine (C—X3-C motif) ligand 1/Hs.531668
CXCL1: Chemokine (C—X—C motif) ligand 1/Hs.789
CXCL10: Chemokine (C—X—C motif) ligand 10/Hs.632586
CXCL11: Chemokine (C—X—C motif) ligand 11/Hs.632592
CXCL12: Chemokine (C—X—C motif) ligand 12/Hs.522891
CXCL13: Chemokine (C—X—C motif) ligand 13/Hs.100431
CXCL14: Chemokine (C—X—C motif) ligand 14/Hs.483444
CXCL16: Chemokine (C—X—C motif) ligand 16/Hs.651206
CXCL2: Chemokine (C—X—C motif) ligand 2/Hs.590921
CXCL3: Chemokine (C—X—C motif) ligand 3/Hs.89690
CXCL5: Chemokine (C—X—C motif) ligand 5/Hs.89714
CXCL6: Chemokine (C—X—C motif) ligand 6/Hs.164021
CXCL9: Chemokine (C—X—C motif) ligand 9/Hs.77367
FAM19A1: Family with sequence similarity 19 (chemokine (C—C motif)-like), member A1/Hs.567895
FAM19A2: Family with sequence similarity 19 (chemokine (C—C motif)-like), member A2/Hs.269745

FAM19A3: Family with sequence similarity 19 (chemokine (C—C motif)-like), member A3/Hs.439116
FAM19A4: Family with sequence similarity 19 (chemokine (C—C motif)-like), member A4/Hs.187873
FAM19A5: Family with sequence similarity 19 (chemokine (C—C motif)-like), member A5/Hs.436854
CKLF: Chemokine-like factor/Hs.15159
XCL1: Chemokine (C motif) ligand 1/Hs.546295
XCL2: Chemokine (C motif) ligand 2/Hs.458346
PPBP: Pro-platelet basic protein (chemokine (C—X—C motif) ligand 7)/Hs.2164
PF4: Platelet factor 4 (chemokine (C—X—C motif) ligand 4)/Hs.81564
Interleukins and Related Proteins
IL10: Interleukin 10/Hs.193717
IL11: Interleukin 11/Hs.467304
IL12A: Interleukin 12A (natural killer cell stimulatory factor 1, p35)/Hs.673
IL12B: Interleukin 12B (natural killer cell stimulatory factor 2, p40)/Hs.674
IL13: Interleukin 13/Hs.845
IL15: Interleukin 15/Hs.168132
IL16: Interleukin 16 (lymphocyte chemoattractant factor)
IL17A: Interleukin 17A/Hs.41724
IL17B: Interleukin 17B/Hs.156979
IL17C: Interleukin 17C/Hs.278911
IL17D: Interleukin 17D/Hs.585624
IL17F: Interleukin 17F/Hs.272295
IL17RE: Interleukin 17 receptor E/Hs.390823
IL18: Interleukin 18 (interferon-gamma-inducing factor)/Hs.83077
IL19: Interleukin 19/Hs.128395
IL1A: Interleukin 1, alpha/Hs.1722
IL1B: Interleukin 1, beta/Hs.126256
IL1F10: Interleukin 1 family, member 10 (theta)/Hs.306974
IL1F5: Interleukin 1 family, member 5 (delta)/Hs.516301
IL1F6: Interleukin 1 family, member 6 (epsilon)/Hs.278910
IL1F7: Interleukin 1 family, member 7 (zeta)/Hs.166371
IL1F8: Interleukin 1 family, member 8 (eta)/Hs.278909
IL1F9: Interleukin 1 family, member 9/Hs.211238
IL1RN: Interleukin 1 receptor antagonist/Hs.81134
IL2: Interleukin 2/Hs.89679
IL20: Interleukin 20/Hs.272373
IL22: Interleukin 22/Hs.287369
IL23A: Interleukin 23, alpha subunit p19/Hs.98309
IL24: Interleukin 24/Hs.58831
IL24: Interleukin 24/Hs.642714
IL25: Interleukin 25/Hs.302036
IL26: Interleukin 26/Hs.272350
IL27: Interleukin 27/Hs.528111
IL28A: Interleukin 28A (interferon, lambda 2)/Hs.567792
IL28B: Interleukin 28B (interferon, lambda 3)/Hs.406744
IL29: Interleukin 29 (interferon, lambda 1)/Hs.406745
IL3: Interleukin 3 (colony-stimulating factor, multiple)/Hs.694
IL31: Interleukin 31/Hs.569071
IL32: Interleukin 32/Hs.943
IL33: Interleukin 33/Hs.348390
IL4: Interleukin 4/Hs.73917
IL5: Interleukin 5 (colony-stimulating factor, eosinophil)/Hs.2247
IL6: Interleukin 6 (interferon, beta 2)/Hs.512234
IL7: Interleukin 7/Hs.591873
IL8: Interleukin 8/Hs.624
IL9: Interleukin 9/Hs.960
LOC723805: Interleukin-like/Hs.644565
LOC728942: Similar to interleukin 28B/Hs.569947
TNF Family Ligands and Related Proteins
APOL3: Apolipoprotein L, 3/Hs.474737
APOL6: Apolipoprotein L, 6/Hs.257352
CD40LG: CD40 ligand (TNF superfamily, member 5)/Hs.592244
CYTL1: Cytokine-like 1/Hs.13872
FASLG: Fas ligand (TNF superfamily, member 6)/Hs.2007
IK: IK cytokine, down-regulator of HLA II/Hs.421245
LITAF: Lipopolysaccharide-induced TNF factor/Hs.459940
LTA: Lymphotoxin alpha (TNF superfamily, member 1)/Hs.36
LTB: Lymphotoxin beta (TNF superfamily, member 3)/Hs.376208
SCYE1: Small inducible cytokine subfamily E, member 1 (endothelial monocyte-activating)/Hs.591680
TNF: Tumor necrosis factor (TNF superfamily, member 2)/Hs.241570
TNFRSF10D: Tumor necrosis factor receptor superfamily, member 10d, decoy with truncated death domain/Hs.213467
TNFRSF1A: Tumor necrosis factor receptor superfamily, member 1A/Hs.279594
TNFSF10: Tumor necrosis factor (ligand) superfamily, member 10/Hs.478275
TNFSF11: Tumor necrosis factor (ligand) superfamily, member 11/Hs.333791
TNFSF13: Tumor necrosis factor (ligand) superfamily, member 13/Hs.54673
TNFSF13B: Tumor necrosis factor (ligand) superfamily, member 13b/Hs.525157
TNFSF14: Tumor necrosis factor (ligand) superfamily, member 14/Hs.129708
TNFSF15: Tumor necrosis factor (ligand) superfamily, member 15/Hs.241382
Peptides Related to Above Categories as Predicted from Transcribed Loci
Transcribed locus, moderately similar to NP_001012039.1 growth factor-containing fibulin-like ECM protein 1 [*Rattus norvegicus*]/Hs.618590
Transcribed locus, moderately similar to NP_071518.1 growth factor 7 [*Rattus norvegicus*]/Hs.629370
Transcribed locus, moderately similar to NP_445880.1 growth factor 13 [*Rattus norvegicus*]/Hs.571674
Transcribed locus, moderately similar to XP_510070.1 similar to Placenta growth factor precursor (P1GF) [Pan troglodytes]/Hs.648773
Transcribed locus, moderately similar to XP_533624.2 similar to Lutropin beta chain precursor (LSH-beta)[*Canis familiaris*]/Hs.569932
Transcribed locus, moderately similar to XP_573983. transforming growth factor, beta induced, 68 kDa [*Rattus norvegicus*]/Hs.620405
Transcribed locus, moderately similar to XP_573983.1 transforming growth factor, beta induced, 68 kDa [*Rattus norvegicus*]/Hs.410773
Transcribed locus, strongly similar to NP_036949.1 growth factor binding protein 5 [*Rattus norvegicus*]/Hs.630151
Transcribed locus, strongly similar to NP_037306.1 growth factor, beta 3 [*Rattus norvegicus*]/Hs.634936
Transcribed locus, strongly similar to NP_037306.1 growth factor, beta 3 [*Rattus norvegicus*]/Hs.637210
Transcribed locus, strongly similar to NP_037306.1 growth factor, beta 3 [*Rattus norvegicus*]/Hs.638602
Transcribed locus, strongly similar to NP_067589.1 growth factor, beta 1 [*Rattus norvegicus*]/Hs.611591

Transcribed locus, strongly similar to NP_067597. transforming growth factor beta binding protein 2 [*Rattus norvegicus*]/Hs.628814

Transcribed locus, strongly similar to NP_071602.1 tissue growth factor [*Rattus norvegicus*]/Hs.644830

Transcribed locus, strongly similar to XP_001125684.1 similar to Amphiregulin precursor (CDGF) [*Homo sapiens*]/Hs.609075

Transcribed locus, strongly similar to XP_527018.1 similar to small inducible cytokine B14 precursor; (BRAK) [Pan troglodytes]/Hs.618286

Transcribed locus, weakly similar to NP_037087.1 hormone primary response protein 1 [*Rattus norvegicus*]/Hs.578013

Transcribed locus, weakly similar to NP_113699.1 growth factor 2 [*Rattus norvegicus*]/Hs.611486

Transcribed locus, weakly similar to XP_001159615.1 chorionic somatomammotropin hormone 2 isoform 49 [Pan troglodytes]/Hs.574913

Transcribed locus, weakly similar to XP_511475.1 similar to IGFBP-4 (IBP-4) (IGF-binding protein 4)[Pan troglodytes]/Hs.626792

Transcribed locus, weakly similar to XP_854800.1 similar to Neurotrophin-5 precursor (NT-5) (Neurotrophin-4) (NT-4)/Hs.598703

Transcribed locus, weakly similar to NP_004855.1 differentiation factor 15 [*Homo sapiens*]/Hs.645113

Others

BAIAP2: BAI1-associated protein 2/Hs.128316
BAIAP2L1: BAI1-associated protein 2-like 1/Hs.584939
BRD8: Bromodomain containing 8/Hs.519337
C1QTNF5: C1q and tumor necrosis factor related protein 5/Hs.632102
CDNA FLJ14109 fis, clone MAMMA1001322, moderately similar to B-CELL GROWTH FACTOR PRECURSOR/Hs.633042
CLEC11A: C-type lectin domain family 11, member A/Hs.512680
CLEC14A: C-type lectin domain family 14, member A/Hs.525307
CSMD2: CUB and Sushi multiple domains 2/Hs.127736
CTTNBP2NL: CTTNBP2 N-terminal like/Hs.485899
EPS8L1: EPS8-like 1/Hs.438862
EPS8L2: EPS8-like 2/Hs.55016
EPS8L3: EPS8-like 3/Hs.485352
HABP2: Hyaluronan binding protein 2/Hs.422542
HECTD1: HECT domain containing 1/Hs.210850
KIAA1822L: KIAA1822-like/Hs.123515
LOC729045: Hypothetical protein LOC729045/Hs.211764
NCLN: Nicalin homolog (zebrafish)/Hs.73797
PPHLN1: Periphilin 1/Hs.444157
PSIP1: PC4 and SFRS1 interacting protein 1/Hs.493516
RHBDF1: Rhomboid 5 homolog 1 (Drosophila)/Hs.57988
SERPINF1: Serpin peptidase inhibitor, Glade F (alpha-2 antiplasmin), member 1/Hs.645378
SLITRK4: SLIT and NTRK-like family, member 4/Hs.272284
SNED1: Sushi, nidogen and EGF-like domains 1/Hs.471834
SPINT1: Serine peptidase inhibitor, Kunitz type 1/Hs.233950
SPINT2: Serine peptidase inhibitor, Kunitz type, 2/Hs.31439
TNFSF10: Tumor necrosis factor (ligand) superfamily, member 10/Hs.478275
TSC22D1: TSC22 domain family, member 1/Hs.507916
TXLNA: Taxilin alpha/Hs.17987

Hormones
Testosterone
Dihydrotestosterone
Androstenedione
Any Androgenic Steroid Hormone
Estrogen
Any Estrogenic Steroid Hormone
Progesterone
Any Progestin or Progestogen The combinations may be administered concurrently, sequentially, or intermittently, once or repeatedly, using various schedules of administration. When used sequentially, the mitogenic agent is preferably administered prior to Auger electron emitting radionuclide, for example $^{125}$IUDR, with an interval of 1-12 hours. Alternatively, the mitogenic agent may be administered as a bolus (brief injection) immediately prior a sustained infusion of $^{125}$IUDR lasting between 5 minutes and 24 hours. Alternatively, the mitogenic agent may be administered as a bolus (brief injection) immediately prior intermittent infusions or injections of $^{125}$IUDR lasting between 1-5 seconds and 1 hour each.

If a growth factor or other mitogenic agent increases the sensitivity of tumor stem cells to the cell killing effects of $^{125}$IUDR, then lower concentrations of $^{125}$IUDR will be required to achieve the same degree of cell death inflicted by $^{125}$IUDR in the absence of the growth factor. Similarly, if a growth factor or other mitogenic agent increases the sensitivity of tumor stem cell to the DNA damaging effects of $^{125}$IUDR, then lower concentrations of $^{125}$IUDR will be required to achieve a comparable degree of DNA damage in the absence of the growth factor. In addition, increased sensitivity to the DNA damaging effects of $^{125}$IUDR might lead to a more steeply sloping radiation kill curve, and increased DNA fragmentation at a given dose of $^{125}$IUDR. The use of growth factors to treat cancer in combination with $^{125}$IUDR should result in a decreased concentration of $^{125}$IUDR required for therapy, a decreased duration of therapy, overall an increased probability of treatment success and to decrease the requirements on the drug delivery reservoir volume.

The inventors herein recognize that combination of mitogenic growth factors and $^{125}$IUDR will make cancer stem cells more susceptible to the DNA damaging effects of $^{125}$IUDR. This is counterintuitive or surprising. First, this approach is distinct from the cell cycle blockade strategy used with success by others (see Clifton, K H et al. Incorporation of $^{125}$I-labeled Iododeoxyuridine into the DNA of Murine and Human tissues following therapeutic doses. Cancer Research 23:1715-1723 (1963); Holmes, J. M. The toxicity of fluorodeoxyuridine when used to increase the uptake of $^{125}$I-iododeoxyuridine into tissue culture cells in vitro. J Comp Pathol. 93:531-539 (1983); F. Buchegger et al Highly efficient DNA incorporation of intratumourally injected [$^{125}$I]-iododeoxyuridine under thymidine synthesis blocking in human glioblastoma xenografts. Int J Cancer 110:145-149 (2004); and Perillo-Adamer, F. Short fluorodeoxyuridine exposure of different human glioblastoma lines induces high-level accumulation of S-phase cells that avidly incorporate $^{125}$I-iododeoxyuridine. Eur J Nucl Med Mol Imaging 33:613-620 (2006). Second, this approach runs counter to the long standing concept that certain mitogenic growth factors (e.g. EGF, KGF, FGF, IGF, VEGF, etc) can promote tumor growth and increase to the risk of toxicity to normal cycling cells. Finally, this overall approach runs contrary to the emerging concept that cell cycle active agents are not well suited for cancer stem cell-directed therapies. For example, see Jordan, C. T. et al. Cancer Stem Cells. N. Eng J. Med. 355:1253-61 (2006). The use of unselective mitogenic agents also runs counter to the current emphasis on the use of targeted agents to treat cancer.

It is known that $^{125}$IUDR is a highly cell cycle active agent that kills only cells actively engaged in DNA synthesis. The more frequently cells are exposed to $^{125}$IUDR the more efficient the cell killing. For example, see Kassis et al. Radiolabeled nucleoside analogs in cancer diagnosis and therapy. The Quarterly Journal of Nuclear Medicine. 40:301-319 (1996); and Adelstein, S J. The Auger Process: a therapeutic Promise? American J. Roentgenology, 160:707-713 (1993). Given the cell cycle dependency of $^{125}$IUDR, optimal killing occurs when it is administered continuously to the cells. Conversely, periodic or episodic exposure of tumor stem cells to $^{125}$IUDR may be less effective than continuous exposure, particularly when used to kill cancer stem cells, which are believed to cycle rather slowly. For example, see Pardal et al. Applying the principles of stem cell biology to cancer. Nature Reviews Cancer 3:895-902 (2003); and Jordan, C. T. et al. Cancer Stem Cells. N. Eng J. Med. 355:1253-61 (2006).

The addition of a growth factor or other mitogenic agent to $^{125}$IUDR can alter its schedule dependency, thereby providing an opportunity to administer $^{125}$IUDR according to a variety of non-continuous dosing schedules with a range of intervals between doses. The addition of a mitogenic agent may provide a novel method by which to kill slowly cycling cancer stem cells using a $^{125}$IUDR, and exquisitely cell cycle active agent.

Effective cell killing by $^{125}$IUDR alone may require continuous exposure, or frequent pulses (several times per day); however, with the addition of a mitogenic growth factor, $^{125}$IUDR may be effective even when the tumor stem cells are exposed only once a day. Different growth factors have potential effects on the cell cycle dependency of $^{125}$IUDR. Preferred growth factors for Glioblastoma multiforme are: EGF, TGF-α, PDGF, basic FGF, FGF2, VEGF, VEGF-C, stem cell factor, Stromal cell-derived factor 1 alpha, DLL-1, DLL-2, DLL-3, JAG-1, Sonic Hedgehog, IGF-1, IGF-2, KGF, HGF, c-kit ligand and granulin.

Mitogens that can be used for cancers outside of the central nervous system (CNS) include:
EGF: epidermal growth factor (beta-urogastrone)/Hs.419815
TGFA: Transforming growth factor, alpha/Hs.170009;
members of the fibroblast growth factor (FGF) family
1FGF1: Fibroblast growth factor 1 (acidic)/Hs.483635
2FGF2: Fibroblast growth factor 2 (basic)/Hs.284244
3FGF3: Fibroblast growth factor 3/Hs.37092
4FGF4: Fibroblast growth factor 4/Hs.1755
5FGF5: Fibroblast growth factor 5/Hs.37055
6FGF6: Fibroblast growth factor 6/Hs.166015
7FGF7: Fibroblast growth factor 7 (keratinocyte growth factor)/Hs.567268
8FGF8: Fibroblast growth factor 8 (androgen-induced)/Hs.57710
9FGF9: Fibroblast growth factor 9 (glia-activating factor)/Hs.111
10FGF10: Fibroblast growth factor 10/Hs.248049
11FGF11: Fibroblast growth factor 11/Hs.380704
12FGF12: Fibroblast growth factor 12/Hs.584758
13FGF13: Fibroblast growth factor 13/Hs.6540
14FGF14: Fibroblast growth factor 14/Hs.651136
16FGF16: Fibroblast growth factor 16/Hs.537037
17FGF17: Fibroblast growth factor 17/Hs.248192
18FGF18: Fibroblast growth factor 18/Hs.87191
19FGF19: Fibroblast growth factor 19/Hs.249200
20FGF20: Fibroblast growth factor 20/Hs.199905
21FGF21: Fibroblast growth factor 21/Hs.283015
22FGF22: Fibroblast growth factor 22/Hs.248087
23FGF23: Fibroblast growth factor 23/Hs.287370
FGFBP1: Fibroblast growth factor binding protein 1/Hs.1690
FGFBP2: Fibroblast growth factor binding protein 2/Hs.98785
FGFBP3: Fibroblast growth factor binding protein 3/Hs.591917
KGFLP1: Keratinocyte growth factor-like protein 1/Hs.439341
KGFLP2: Keratinocyte growth factor-like protein 2/Hs.652376
LOC728195: Similar to KGF precursor (Fibroblast growth factor 7) (HBGF-7)/Hs.648152
PDGFA: Platelet-derived growth factor alpha polypeptide/Hs.645488
PDGFB: Platelet-derived growth factor beta polypeptide/Hs.1976
PDGFC: Platelet derived growth factor C/Hs.570855
PDGFD: Platelet derived growth factor D/Hs.352298
LOC729619: Similar to Platelet-derived growth factor A chain precursor (PDGF A-chain) (PDGF-1)/Hs.632644
KITLG: KIT ligand/Hs.1048
HBEGF: Heparin-binding EGF-like growth factor/Hs.799
HGF: Hepatocyte growth factor (hepapoietin A; scatter factor)/Hs.396530
MST1: Macrophage stimulating 1 (hepatocyte growth factor-like)/Hs.349110
HDGF: Hepatoma-derived growth factor (high-mobility group protein 1-like)/Hs.506748
HDGF2: Hepatoma-derived growth factor-related protein 2/Hs.43071
HDGFL1: Hepatoma derived growth factor-like 1/Hs.97124
HDGFRP3: Hepatoma-derived growth factor, related protein 3/Hs.513954
LOC727738: Similar to Amphiregulin precursor (AR) (Colorectum cell-derived growth factor)/Hs.645475
AREG: Amphiregulin (schwannoma-derived growth factor)/Hs.270833
CTGF: Connective tissue growth factor/Hs.591346
TDGF1: Teratocarcinoma-derived growth factor 1/Hs.385870
GFER: Growth factor (ERV1 homolog, *S. cerevisiae*)/Hs.27184
GFI1: Growth factor independent 1/Hs.73172
EGFL6: EGF-like-domain, multiple 6/Hs.12844
VEGFA: Vascular endothelial growth factor A/Hs.73793
VEGFB: Vascular endothelial growth factor B/Hs.78781
VEGFC: Vascular endothelial growth factor C/Hs.435215
VGF: VGF nerve growth factor inducible/Hs.587325
PGF: Placental growth factor, vascular endothelial growth factor-related protein/Hs.252820
FIGF: C-fos induced growth factor (vascular endothelial growth factor D)/Hs.11392
ECGF1: Endothelial cell growth factor 1 (platelet-derived)/Hs.592212
CYR61: Cysteine-rich, angiogenic inducer, 61/Hs.8867
IGF1: Insulin-like growth factor 1 (somatomedin C)/Hs.160562
IGF2: Insulin-like growth factor 2 (somatomedin A)/Hs.373908
IGFALS: Insulin-like growth factor binding protein, acid labile subunit/Hs.839
IGFBP1: Insulin-like growth factor binding protein 1/Hs.642938
IGFBP2: Insulin-like growth factor binding protein 2, 36 kDa/Hs.438102
IGFBP3: Insulin-like growth factor binding protein 3/Hs.450230
IGFBP4: Insulin-like growth factor binding protein 4/Hs.462998

IGFBP5: Insulin-like growth factor binding protein 5/Hs.635441
IGFBP6: Insulin-like growth factor binding protein 6/Hs.274313
IGFBP7: Insulin-like growth factor binding protein 7/Hs.479808
IGFBPL1: Insulin-like growth factor binding protein-like 1/Hs.349705
IGFL1: IGF-like family member 1/Hs.546554
IGFL2: IGF-like family member 2/Hs.99376
IGFL3: IGF-like family member 3/Hs.365496
IGFL4: IGF-like family member 4/Hs.531310
INSL3: Insulin-like 3/Hs.37062
INSL4: Insulin-like 4 (placenta)/Hs.418506
INSL5: Insulin-like 5/Hs.251380
INSL6: Insulin-like 6/Hs.632648
RLN3: Relaxin 3/Hs.352155
A growth factor that stimulates cancer stem cells to enter into S-phase
A growth factor that stimulates transit-amplifying cancer cells (or cancer progenitor cells) to enter into S-phase.

Mitogenic steroids that can be used in various embodiments of the inventive method for treatment of prostate cancer include: testosterone, dihydrotestosterone, androstenedione, or any androgenic steroid hormone; withdrawal of androgen blockade by anti-androgens (flutamide, nilutamide and bicalutamide) or inhibitors of the 5-alpha-reductase (e.g. finasteride and dutasteride).

Mitogenic steroids that can be used in various embodiments of the inventive method for treatment of ovarian, breast and endometrial cancers include: Estrogen, progesterone, or any estrogenic steroid or progestin.

At the present time, no treatments are known to reliably and effectively kill cancer stem cells in solid tumors. The use of a mitogenic protein, when combined with $^{125}$IUDR can provide a method by which to effectively kill any type of cycling cells, in particular cancer stem cells and transit-amplifying cancer cells. The combination of a mitogenic growth factor plus $^{125}$IUDR can provide a method to kill cancer stem cells using a variety of episodic or periodic schedules of administration. First, continuous delivery of $^{125}$IUDR to the tumor may be less impractical than intermittent delivery. Constant delivery requires a pump, a sustained release polymer or other drug delivery device, to continuously deliver $^{125}$IUDR into the tumor. This requires not only constant release, but also a volume of infusate that is larger than required by intermittent delivery. Thus, intermittent delivery may provide a method by which $^{125}$IUDR can not only kill the cancer stem cells more efficiently, but also the ability to do so using smaller total volumes of infusate, shorter durations of therapy and possibly increased success of treatment. Intermittent administration of $^{125}$IUDR would also be more convenient for healthcare workers and the patients.

An important recent development is the realization that tumor stem cells are not distributed randomly in GBM tumors; indeed, tumor stem cells reside in "vascular niches", and their survival and ongoing proliferation depends upon trophic factors (e.g. VEGF) secreted by vascular endothelial cells that are immediately adjacent to the tumor stem cells. For example see Calabrese C et al. A perivascular niche for brain tumor stem cells. Cancer Cell 11:69-82 (2007). Disruption of the vascular endothelium using antibodies directed at VEGF leads to tumor shrinkage in these models (also see Bao S. et al. Stem cell-like glioma cells promote tumor angiogenesis through vascular endothelial growth factor. Cancer Res. 66:7843-7848 [2006]). Thus, it is possible to indirectly disrupt or inhibit the growth of brain tumor stem cells (BTSC) by targeting the blood vessels that sustain these cells. Tumor associated blood vessels can be disrupted by numerous anti-angiogenic agents, including antibodies that block the effects of VEGF. For example see Fidler I. J. et al. "Angiogenesis" pp 129-136 in Cancer Principles and Practice of Oncology 7$^{th}$ edition. De Vita V T, Hellmann S and Rosenberg S A. Lippincott Williams & Wilkins © 2005). In this disclosure we suggest that $^{125}$IUDR be used to disrupt the "vascular niches" needed for the survival and ongoing proliferation of BTSC. It is possible to use VEGF to induce vascular growth in these niches to accelerate the elimination of such niches and increase the probability of the elimination of the cancer stem cells.

The growth of certain malignancies, such as cancers of the prostate, breast and ovaries are known to be stimulated by sex steroid hormones, and they are inhibited by compounds that block the actions of the sex steroids. For example, estrogens stimulate the proliferation of hormone receptor positive breast cancer, endometrial and ovarian cancers, while anti-estrogens (e.g. tamoxifen, raloxifene, toremifene) and aromatase inhibitors (e.g. anastrozole), exemestane and letrozole) can inhibit cell proliferation in many of these cancers. Similarly, the administration of testosterone, androstenedione or dihydrotestosterone stimulates the proliferation of hormone-sensitive prostate cancer, while treatment with antiandrogens (e.g. flutamide, nilutamide and bicalutamide) and inhibitors of the 5-alpha-reductase enzyme (e.g. finasteride and dutasteride) can block cell proliferation in these cancers. Hormone sensitive prostate and breast cancers may also be inhibited by interfering with the hypothalamic-pituitary-gonadal axis using a gonadotropin-releasing hormone analogue such as leuprolide acetate; this is indirect blockade.

In the case of prostate cancer, once the androgen withdrawal or androgen blockade ceases, testosterone becomes available to stimulate the prostate cancer cells, which may synchronously enter the S-phase of the cell cycle. Thus, by using a sequence of androgen blockade followed by androgen exposure, it is possible to stimulate waves of DNA synthesis within a population of prostate cancer cells. Thus, steroid hormones, drugs and gonadotropin-releasing hormone analogues such as leuprolide acetate, can be used to manipulate the cell cycle of cells of certain types of cancers. Using such pharmacological manipulations; it is possible to stimulate certain types of cancer cells to replicate their DNA and thereby enter S-phase of the cell cycle. Because of the mechanism of action of the radioactive agent such as $^{125}$IUDR, any diseases that have a component of excess tissue proliferation are candidates for therapy. The best candidate is cancer, but other proliferative diseases can be treated with this therapy such as macular degeneration, psoriasis, benign prostatic hyperplasia, proliferative vitreo retinopathy (fibroblastic infiltration into the vitreous), or vascular intimal hyperplasia. All of these diseases have components of localized inappropriately proliferating cells causing the disease. An agent such as $^{125}$IUDR would be able to kill these excessively dividing cells and ameliorate the disease process.

The inventors herein have also recognized that use of a radiotherapeutic agent characterized by a short-range cytotoxic radioactive emission, like $^{125}$IUDR, can be used in the treatment of noncancerous proliferative disorders. In the treatment noncancerous proliferative disorders of cells, such as AMD, proliferative vitreoretinopathy, or benign prostatic hypertrophy, various embodiments of the inventive method can be used to stop neo-vascularization by killing dividing vascular endothelial cells. Accordingly, it is recognized that treatment of macular degeneration with $^{125}$IUDR will kill proliferating vascular endothelial cells and successfully treat AMD. Various embodiments of the inventive method provide for treatment of noncancerous proliferative disorders by administration of the radiotherapeutic agent, which can be administered selectively to a volume of tissue comprising the hyperproliferative cells; in the case of AMD, the area of the retina.

Unexpectedly, the inventors herein have also recognized that the use of growth factors in the treatment of noncancerous hyperproliferative diseases such as AMD is advantageous, although it is generally believed in the art that the use of growth factors should be avoided as likely to enhance the disease process. However, according to various embodiments in the inventive method herein, the use of a growth factor that stimulates the cell division of the abnormal growth of the vascular endothelial cells (such as VEGF) will increase the incorporation of the $^{125}$IUDR into the hyperproliferative cells, and thereby eliminate the cells quickly, allowing for a shorter duration of therapy.

The inventors herein recognize that the use of various embodiments of the radiotherapeutic agent, such as $^{125}$IUDR, can be administered to kill the proliferating vascular endothelial cells via intravitreal injection. Administration into the vitreus would expose the proliferating vascular endothelial cells that have grown through Bruch's membrane and are the major target for treatment in "wet" AMD. However, it is believe by the inventors herein that there should be no effect on the retina, since radiotherapeutic agents such as $^{125}$IUDR will not effectively penetrate Bruch's membrane.

In various embodiments of the invention, a catheter or a plurality of catheters can be used in conjunction with a pump and a reservoir to deliver the radiotherapeutic agent, the mitogenic agent, or both, to the vitreous, using a continuous or intermittent drug delivery profile to maximize efficacy. For example, $^{125}$IUDR can be infused alone or in combination with a mitogenic agent that facilitates endothelial proliferation such as VEGF.

In various embodiments of the invention, a catheter or a plurality of catheters can be used in conjunction with a pump and a reservoir to deliver the radiotherapeutic agent, the mitogenic agent, or both, to the sclera, as a route of entry into the vitreous, for example using a continuous or intermittent drug delivery profile to maximize therapeutic benefit.

A radiotherapeutic agent as defined herein, for example $^{125}$IUDR, can be used alone as an effective treatment, as well as in combination with a mitogenic agent that will enhance cell division in the target tissue. For example, in an embodiment, treatment of macular degeneration can include localized delivery, use of $^{125}$IUDR to eliminate any dividing cells (specifically any vascular endothelial cells that have grown through Bruch's membrane). Further it is then possible to combine the use of $^{125}$IUDR to eliminate any dividing cells with the use of mitogens to shorten duration of therapy and increase efficacy by inducing the target cells to divide and incorporate the $^{125}$IUDR. As with other applications of this drug the scheduling and duration of therapy can be critical. In general the scheduling needs to be adjusted to ensure that target cells are exposed during a period of DNA replication and minimize the chances that target cells escape incorporation of the $^{125}$IUDR into their DNA.

In various embodiments of the invention, the radiotherapeutic agent can be infused with or without the mitogenic agent, for example according to a schedule that is disclosed hereunder. The agent(s) can be discharged continuously from a catheter or a plurality thereof into the tissues as a result of a pressure gradient that can be generated and maintained by an infusion pump. In the latter case, the pressure gradient can be maintained throughout the delivery of the agent, thereby producing continuous bulk flow (convection enhanced delivery) of the agent(s) into the tissue. The fluid pressure may be increased in one or more steps, increased continuously over at least part of the infusion period, or increased over all of the entire infusion period.

The agent(s), i.e., the radiotherapeutic agent, the mitogenic agent, or both, can be infused for duration of at least 15 minutes; for 1 hour; for 2 hours; for 4 hours; for 6 hours; for 8 hours; for 10 hours; for 12 hours; or for 24 hours; Alternatively, the agent(s) may be infused continuously for 2 days; for 7 days; for 14 days; for 28 days; for 56 days; for 180 days; or for 365 days. In addition, the agent(s) may be infused for a duration of less than one hour if the treatment is located outside the brain. For example in the case of macular degeneration, the injection may be simple intermittent bolus injections.

The agent(s) may be discharged repetitively or intermittently from the catheter or catheters into the tissues as a result of fluid pressure generated by the infusion pump. The increased fluid pressure may be instantaneous or brief in duration, thereby producing a rapid infusion of the agent(s) into the tissue. Alternatively, the pressure gradient may be more sustained, but not maintained continuously throughout the delivery of the agent, thereby producing one or more fluid waves that carry the agent(s) into the tissue. In either case, the intervals between the repetitive or intermittent discharges of fluid may be brief (e.g. one second) or longer (e.g. several hours or several days). The latter are examples of pulsed delivery of the fluid pharmacological agent into tissue.

The agent(s) can be infused using various repetitive intermittent schedules of administration. For example the agent(s) may be infused for 2 hours followed by an interval of 2 hours during which the infusion is stopped; or for 2 hours followed by an interval of 4 hours without infusion; or for 2 hours followed by an interval of 6 hours without infusion; or for 2 hours followed by an interval of 8 hours without infusion; or for 2 hours followed by an interval of 10 hours without infusion; or for 2 hours followed by an interval of 12 hours without infusion.

Alternatively, the agent(s) can be infused for 4 hours followed by an interval of 4 hours during which the infusion is stopped; or for 4 hours followed by an interval of 6 hours without infusion; or for 4 hours followed by an interval of 8 hours without infusion; or for 4 hours followed by an interval of 10 hours without infusion; or for 4 hours followed by an interval of 12 hours without infusion.

Alternatively, the agent(s) can be infused for 6 hours followed by an interval of 6 hours during which the infusion is stopped; or for 6 hours followed by an interval of 8 hours without infusion; or for 6 hours followed by an interval of 10 hours without infusion; or for 6 hours followed by an interval of 12 hours without infusion.

Alternatively, the agent(s) can be infused for 8 hours followed by an interval of 6 hours during which the infusion is stopped; or for 8 hours followed by an interval of 8 hours without infusion; or for 8 hours followed by an interval of 10 hours without infusion; or for 8 hours followed by an interval of 12 hours without infusion.

Alternatively, the agent(s) can be infused for 10 hours followed by an interval of 6 hours during which the infusion is stopped; or for 10 hours followed by an interval of 8 hours without infusion; or for 10 hours followed by an interval of 10 hours without infusion; or for 10 hours followed by an interval of 12 hours without infusion.

Alternatively, the agent(s) can be infused for 12 hours followed by an interval of 6 hours during which the infusion is stopped; or for 12 hours followed by an interval of 8 hours without infusion; or for 12 hours followed by an interval of 10 hours without infusion; or for 12 hours followed by an interval of 12 hours without infusion.

According to another embodiment of the invention, the agent(s) can be discharged as a brief injection, a pulse, or as a more sustained infusion into the tissues, and then followed by an infusion of fluid that does not contain the agent(s). The fluid lacking an agent may be introduced into the tissue by one or more instantaneous injections, one or more sustained waves of fluid movements, or by continuous bulk flow that is maintained by a constant pressure gradient.

A fluid adapted for infusion of the radiotherapeutic agent, which can be $^{125}$IUDR, $^{123}$IUDR, or a related radioactive nucleoside analog, can contain the agent at a concentration between 1 picomole/liter (1 pM) and 1 millimole/liter (1 mM); or the fluid may contain such compounds at concentrations between 1picomole/liter (1 pM) and 500 micromole/liter (500uM); or the fluid may contain such compounds at concentrations between 1 picomole/liter (1pM) and 50 micromole/liter (50 uM); or the fluid may contain such compounds at concentrations between 1 picomole/liter (1 pM) and 10 micromoles/liter (10 uM); or the fluid may contain such compounds at concentrations between 1 picomole/liter (1 pM) and 1 micromoles/liter (1 uM); or the fluid may contain such compounds at concentrations between 1 picomole/liter (1 pM) and 500 nanomoles/liter (500 nM); or the fluid may contain such compounds at concentrations between 1 picomole/liter (1 pM) and 50 nanomoles/liter (50 nM); or the fluid may contain such compounds at concentrations between 1 picomole/liter (1 pM) and 10 nanomoles/liter (10 nM); or the fluid may contain such compounds at concentrations between 1 picomole/liter (1 pM) and 1 nanomoles/liter (1 nM); or the fluid may contain such compounds at concentrations between 1 and 500 picomole/liter (1 pM-500 pM); or the fluid may contain such compounds at concentrations between 1 and 50 picomole/liter (1 pM-50 pM); or the fluid may contain such compounds at concentrations between 1 and 10 picomole/liter (1 pM-10 pM).

The solution or suspension containing the Auger-electron emitting radionucleoside can contain further constituents, such as liposomes, surfactants, salts, and the like. The solution or suspension can also include additional medicinal substances for delivery to the afflicted tissue, such as anti-inflammatories, antibiotics, and the like. The solution or suspension can also be incorporated, for example, into bioerodible filaments, other forms of biodegradable polymers such a depots, and the like. As discussed above, the solution or suspension containing the radiotherapeutic agent can be administered via a catheter or a plurality thereof, by convection enhanced delivery, and the like.

Additional References

R. Bhargava et al., "EGFR gene amplification in breast cancer: correlation with epidermal growth factor receptor mRNA and protein expression and HER-2 status and absence of EGFR-activating mutations," Modern Pathology 18:1027-1033 (2005)

T. Baron et al., "Serum sErbB1 and Epidermal Growth Factor Levels As Tumor Biomarkers in Women with Stage III or IV Epithelial Ovarian Cancer," Cancer Epidemiology Biomarkers & Prevention, 8: 129-137 (1999)

H Kothmaier et al., "EGFR and PDGFR differentially promote growth in malignant epithelioid mesothelioma of short and long term survivors," Thorax, 63:345-351 (2008)

M. P. DiGiovanna et al., "Relationship of Epidermal Growth Factor Receptor Expression to ErbB-2 Signaling Activity and Prognosis in Breast Cancer Patients," *Journal of Clinical Oncology*, 23: 1152-1160 (2005)

K. Cho et al, "Enhanced expression of keratinocyte growth factor and its receptor correlates with venous invasion in pancreatic cance," American Journal of Pathology, 170: 1964-74 (2007)

T. Ishiwata, et al., "Characterization of keratinocyte growth factor and receptor expression in human pancreatic cancer," American Journal of Pathology, 153:213-22 (1998)

A. L. Ogilvy-Stuart and H. Gleeson, "Cancer risk following growth hormone use in childhood: implications for current practice," Drug Safety, 27:369-82 (2004)

P. J. Jenkins et al., "Does growth hormone cause cancer?" Clinical Endocrinology, 64:115-21 (2006)

P. Cohen, D. R. Clemmons and R. G. Rosenfeld, "Does the GH-IGF axis play a role in cancer pathogenesis" Growth Hormone and IGF Research, 10: 297-305 (200).

S. M. Shalet, B. M. Brennan and R. E. Reddingius. "Growth hormone therapy and malignancy," Hormone Research, 48: 29-32 (1997)

Sachdev D, Yee D, "Disrupting insulin-like growth factor signaling as a potential cancer therapy," Molecular Cancer Therapy, 6:1-12 (2007)

D. LeRoith and C. T. Roberts, "The insulin-like growth factor system and cancer," Cancer Letters, 195:127-37 (2003)

Pollak M, Beamer W, Zhang J C, "Insulin-like growth factors and prostate cancer," Cancer Metastasis Reviews, 17:383-90 (1998)

L. Tentori and G. Graziani, "Doping with growth hormone/IGF-1, anabolic steroids or erythropoietin: is there a cancer risk?" Pharmacology Research, 55:359-69 (2007)

M. Pollak "Insulin-like growth factor-related signaling and cancer development," Recent Results in Cancer Research, 174:49-53 (2007)

Fürstenberger G, Morant R, Senn H J. "Insulin-like growth factors and breast cancer," Onkologie, 26:290-4 (2003)

E. Giovannucci, "." Insulin-like growth factor-I and binding protein-3 and risk of cancer," Hormone Research, 3:34-41 (1991)

A. G. Renehan et al., "Insulin-like growth factor (IGF)-I, IGF binding protein-3, and cancer risk: a systematic review and meta-regression analysis," Lancet, 363:1346-53 (2004)

E. E. Vokes and E. Chu "Anti-EGFR therapies: clinical experience in colorectal, lung, and head and neck cancers," *Oncology*, 20:15-25 (2006)

S. F. Wong, "Cetuximab: an epidermal growth factor receptor monoclonal antibody for the treatment of colorectal cancer," Clinical Therapeutics, 7:684-94 (2005)

E. Tokunaga et al., "Trastuzumab and breast cancer: developments and current status," International Journal of Clinical Oncology, 11:199-208 (2006).

I. K. Mellinghoff, et al., "Molecular Determinants of the Response of Glioblastomas to EGFR Kinase Inhibitors," New England Journal of Medicine, 353:2012-24 (2005)

N. Ferrara, "Role of vascular endothelial growth factor in physiologic and pathologic angiogenesis: therapeutic implications," Seminars in Oncology, 29:10-4 (2002).

S. Shinkaruk et al., "Vascular endothelial cell growth factor (VEGF), an emerging target for cancer chemotherapy," Curr Med Chem Anticancer Agents," 3:95-117 (2003)

J. Hackett et al., "Development of keratinocyte growth factor receptor tyrosine kinase inhibitors for treatment of cancer," Anticancer Research, 27:3801-6 (2007).

Y. Feng and D. S. Dimitrov, "Monoclonal antibodies against components of the IGF system for cancer treatment" Current Opinion in Drug Discovery and Development," 112: 178-85 (2008)

D. S. Krause, et al., "Tyrosine Kinases as Targets for Cancer Therapy," New England Journal of Medicine, 353:172-87 (2005)

M. C. Bosland, "The role of steroid hormones in prostate carcinogenesis," Journal of the National Cancer Institute Monograph, 27:39-66 (2000)

J. V. Lacey et al., "Menopausal hormone replacement therapy and risk of ovarian cancer," Journal of the American Medical Association, 288:334-41 (2002)

J. D. Debes and D. J. Tindall, "The role of androgens and the androgen receptor in prostate cancer," Cancer Letters, 187: 1-7 (2002)

E. A. Platz and E. Giovannucci, "The epidemiology of sex steroid hormones and their signaling and metabolic pathways in the etiology of prostate cancer," Journal of Steroid Biochemistry and Molecular Biology, 92:237-53 (2004)

J. L. Hecht and G. L. Mutter, "Molecular and pathologic aspects of endometrial carcinogenesis," Journal of Clinical Oncology, 24:4783-91 (2006)

J. G. Reeder and V. G. Vogel, "Breast cancer risk management," Clinical Breast Cancer, 7:833-40 (2007)

W. Shelly et al., "Selective estrogen receptor modulators: an update on recent clinical findings. Obstetrics and Gynecology Surveys," 63:163-81 (2008)

H. L. Parnes et al., "Prevention of hormone-related cancers: prostate cancer," Journal of Clinical Oncology," 23:368-77 (2005).

Brodie A, Sabnis G, Jelovac D. "Aromatase and breast cancer," Journal of Steroid Biochemistry and Molecular Biology, 102:97-102 (2006).

C. J. Fabian, "Chemoprevention for high-risk women: tamoxifen and beyond," Breast Journal, 7:311-20 (2001).

What is claimed is:

1. A method of treatment of a malcondition characterized by cancer cells in a patient, comprising sequentially administering to a tissue of the patient comprising the cancer cells a mitogenic agent comprising an androgenic a steroidal hormone to induce the cancer cells to enter into S phase, followed, after one hour or more, by administration of a radiotherapeutic Auger electron-emitting nucleoside analog or prodrug thereof, wherein the Auger electron-emitting nucleoside analog or prodrug thereof is administered systemically to the patient, or is administered selectively to a volume of tissue of the patient using convection enhanced delivery.

2. The method of claim 1 wherein both the mitogenic steroid, and the Auger electron-emitting nucleoside analog or prodrug thereof, are administered systemically to the patient.

3. The method of claim 1 wherein both the mitogenic steroid, and the Auger electron-emitting nucleoside analog or prodrug thereof, are administered selectively to a volume of tissue of the patient using convection enhanced delivery, optionally comprising use of bioerodible filaments, a catheter, an array of catheters, or any combination thereof.

4. The method of claim 1 wherein the mitogenic steroid is administered systemically to the patient and the Auger electron-emitting nucleoside analog or prodrug thereof is administered selectively to a volume of tissue of the patient using convection enhanced delivery, optionally comprising use of bioerodible filaments, a catheter, an array of catheters, or any combination thereof.

5. The method of claim 1 wherein the cancer cells are comprised by a solid tumor.

6. The method of claim 5 wherein the solid tumor is an advanced stage solid tumor.

7. The method of claim 5 wherein the solid tumor is at an early stage.

8. The method of claim 6 wherein the solid tumor proliferates in response to one or more steroid hormones.

9. The method of claim 7 wherein the solid tumor proliferates in response to one or more steroid hormones.

10. The method of claim 5 wherein the solid tumor is prostatic cancer.

11. The method of claim 1 wherein administering to the spatially restricted volume of tissue comprises intratumoral or peritumoral administration.

12. The method of claim 1 wherein the Auger electron-emitting nucleoside analog or prodrug thereof comprises $^{77}$Br, $^{80m}$Br, $^{123}$I, $^{124}$I, $^{125}$I, or $^{221}$At.

13. The method of claim 1 wherein the Auger electron-emitting nucleoside analog or prodrug thereof comprises a halogenated nucleoside analog.

14. The method of claim 1 wherein the Auger electron-emitting nucleoside analog or a prodrug thereof comprises a prodrug of a halogenated nucleoside analog comprising a 3' or a 5' carboxylate or phosphate ester of the halogenated nucleoside analog.

15. The method of claim 1, wherein the steroidal hormone comprises testosterone, dihydrotestosterone, androstenedione, an androgenic steroid hormone, or any combination thereof.

16. The method of claim 1 wherein the halogenated nucleoside analog comprises 5-[$^{123}$I]iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine 2'-deoxyribonucleoside, 5-[$^{211}$At]-astatouridine 2'-deoxyribonucleoside, or 8-[$^{211}$At]-astatoadenine 2'-deoxyribonucleoside.

17. The method of claim 1 wherein the prodrug of the halogenated nucleoside analog comprises a 3' or a 5' carboxylate or phosphate ester of any of 5-[$^{123}$I]-iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine 2'-deoxyribonucleoside, 5-[$^{211}$At]-astatouridine 2'-deoxyribonucleoside, or 8-[$^{211}$At]-astatoadenine 2'-deoxyribonucleoside.

18. The method of claim 1 wherein the Auger electron-emitting nucleoside analog or prodrug thereof is incorporated into DNA of a cancer cell.

19. The method of claim 1 wherein administering the Auger electron-emitting nucleoside analog or prodrug thereof comprises administering continuously over a over a period of time, intermittently, on a regular schedule, or any combination thereof.

20. The method of claim 1 wherein administering comprises administering in an intermittent, repetitive, or pulsatile manner.

21. The method of claim 1, further comprising administering an additional medicament to the patient.

22. The method of claim 21 wherein the additional medicament comprises an anticancer drug, an anti-inflammatory drug, or an antibiotic, or a combination thereof.

* * * * *

UNITED STATES PATENT AND TRADEMARK OFFICE
CERTIFICATE OF CORRECTION

PATENT NO. : 8,470,295 B2
APPLICATION NO. : 12/599594
DATED : June 25, 2013
INVENTOR(S) : Warren et al.

It is certified that error appears in the above-identified patent and that said Letters Patent is hereby corrected as shown below:

On Title page 2, item [56] in column 1, under "Other Publications", line 22, delete "S," and insert --S.,--, therefor On Title page 2, item [56] in column 2, under "Other Publications", line 29, delete "F," and insert --F.,--, therefor On Title page 2, item [56] in column 2, under "Other Publications", line 33, delete "[125I]" and insert --[$^{125}$I]--, therefor On Title page 2, item [56] in column 2, under "Other Publications", line 36, delete "A," and insert --A.,--, therefor On Title page 2, item [56] in column 2, under "Other Publications", line 40, delete "S," and insert --S.,--, therefor In the Claims Column 27, line 37, Claim 1, after "androgenic", delete "a", therefor Column 28, line 14, Claim 12, delete "$^{221}$At" and insert --$^{211}$At--, therefor Column 28, line 28, Claim 16, delete "5-[$^{123}$I]iodouridine" and insert --5-[$^{123}$I]-iodouridine--, therefor Column 28, line 29, Claim 16, delete "5-[$^{124}$I]-iodouridine" and insert --5-[$^{124}$I]-iodouridine--, therefor Column 28, line 32, Claim 16, delete "8 -[$^{123}$I]-iodoadenine" and insert --8-[$^{123}$I]-iodoadenine--, therefor Signed and Sealed this
Thirteenth Day of May, 2014

Michelle K. Lee
*Deputy Director of the United States Patent and Trademark Office*

Column 28, line 39, Claim 17, delete "5 -[$^{123}$I]-iodouridine" and insert --5-[$^{123}$I]-iodouridine--, therefor Column 28, line 53, Claim 19, after "continuously", delete "over a", therefor

UNITED STATES PATENT AND TRADEMARK OFFICE
CERTIFICATE OF CORRECTION

PATENT NO. : 8,470,295 B2  Page 1 of 1
APPLICATION NO. : 12/599594
DATED : June 25, 2013
INVENTOR(S) : Warren et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this
Eighth Day of September, 2015

Michelle K. Lee
*Director of the United States Patent and Trademark Office*